United States Patent
Shinaoka et al.

(10) Patent No.: US 11,246,948 B2
(45) Date of Patent: Feb. 15, 2022

(54) METHOD OF EVALUATING LYMPHATIC SYSTEM FUNCTION

(71) Applicants: National University Corporation Okayama University, Okayama (JP); HAMAMATSU PHOTONICS K.K., Hamamatsu (JP)

(72) Inventors: Akira Shinaoka, Okayama (JP); Yoshihiro Kimata, Okayama (JP); Aiji Ohtsuka, Okayama (JP); Takahiro Shikayama, Hamamatsu (JP)

(73) Assignees: National University Corporation Okayama University, Okayama (JP); HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 16/236,722

(22) Filed: Dec. 31, 2018

(65) Prior Publication Data

US 2019/0201555 A1  Jul. 4, 2019

Related U.S. Application Data

(60) Provisional application No. 62/613,508, filed on Jan. 4, 2018, provisional application No. 62/687,268, filed on Jun. 20, 2018, provisional application No. 62/727,637, filed on Sep. 6, 2018, provisional application No. 62/771,648, filed on Nov. 27, 2018.

(30) Foreign Application Priority Data

Nov. 21, 2018  (JP) .............................. JP2018-218536

(51) Int. Cl.
| | |
|---|---|
| *A61B 5/00* | (2006.01) |
| *A61K 49/04* | (2006.01) |
| *A61K 49/00* | (2006.01) |
| *A61B 6/00* | (2006.01) |
| *A61B 6/03* | (2006.01) |

(52) U.S. Cl.
CPC .......... *A61K 49/0034* (2013.01); *A61B 5/418* (2013.01); *A61B 6/481* (2013.01); *A61B 6/50* (2013.01); *A61K 49/0071* (2013.01); *A61K 49/04* (2013.01); *A61K 49/0438* (2013.01); *A61K 49/0452* (2013.01); *A61B 6/032* (2013.01); *A61B 6/037* (2013.01)

(58) Field of Classification Search
None
See application file for complete search history.

(56) References Cited

PUBLICATIONS

Tan et al. Assessment of lymphatic contractile function after manual lymphatic drainage using near-infrared fluorescence imaging. 2011 Arch. Phys. Med. Rehabil. 92: 756-764. (Year: 2011).*

Maegawa, Jiro, et al., "Types of Lymphoscintigraphy and Indications for Lymphaticovenous Anastomosis," Microsurgery, 30(6), 2010, pp. 437-442.

Unno, Naoki, et al., "Preliminary experience with a novel fluorescence lymphography using indocyanine green in patients with secondary lymphedema," Journal of Vascular Surgery, 45(5), 2007, pp. 1016-1021.

* cited by examiner

*Primary Examiner* — Jennifer Lamberski

(74) *Attorney, Agent, or Firm* — Faegre Drinker Biddle & Reath LLP

(57) ABSTRACT

An embodiment relates to a method of evaluating a lymphatic system function including: selecting one or a plurality of lymphatic routes to be evaluated from a plurality of lymphatic routes existing in four limbs; determining an injection site of a visualization agent based on information on the selected lymphatic route and injection sites of peripheries of the four limbs corresponding to the selected lymphatic route; injecting the visualization agent from the selected injection site; and visualizing the injected visualization agent and evaluating functions of the one or plurality of lymphatic routes to be evaluated.

5 Claims, 40 Drawing Sheets

▧ AM: ANTEROMEDIAL ROUTE
▨ AL: ANTEROLATERAL ROUTE
▩ PL: POSTEROLATERAL ROUTE
▭ PM: POSTEROMEDIAL ROUTE

——— AM: ANTEROMEDIAL ROUTE
—·— PL: POSTEROLATERAL ROUTE
——— AL: ANTEROLATERAL ROUTE
········· PM: POSTEROMEDIAL ROUTE

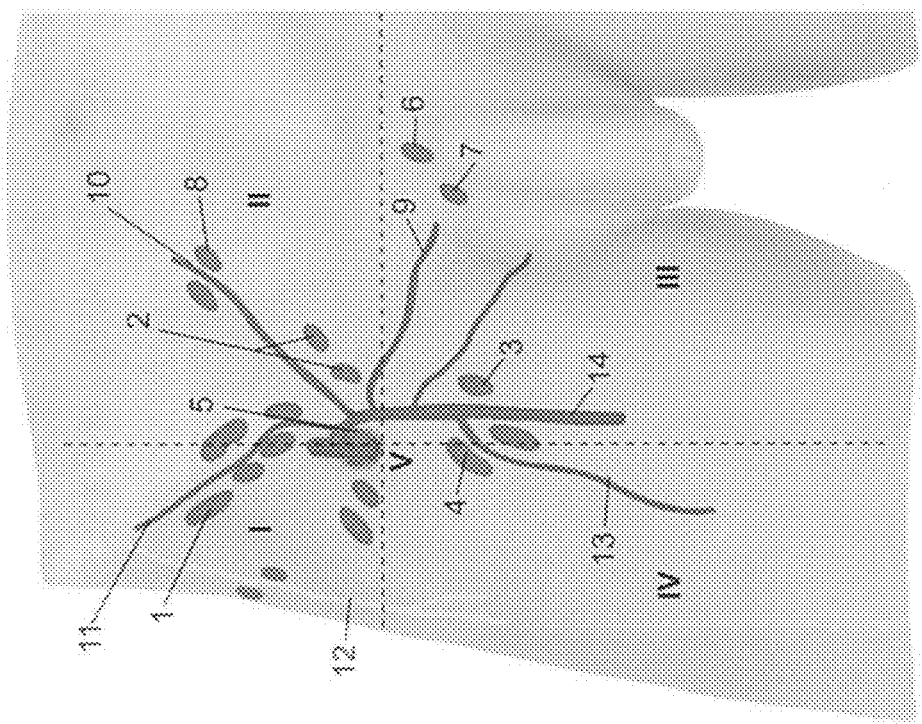
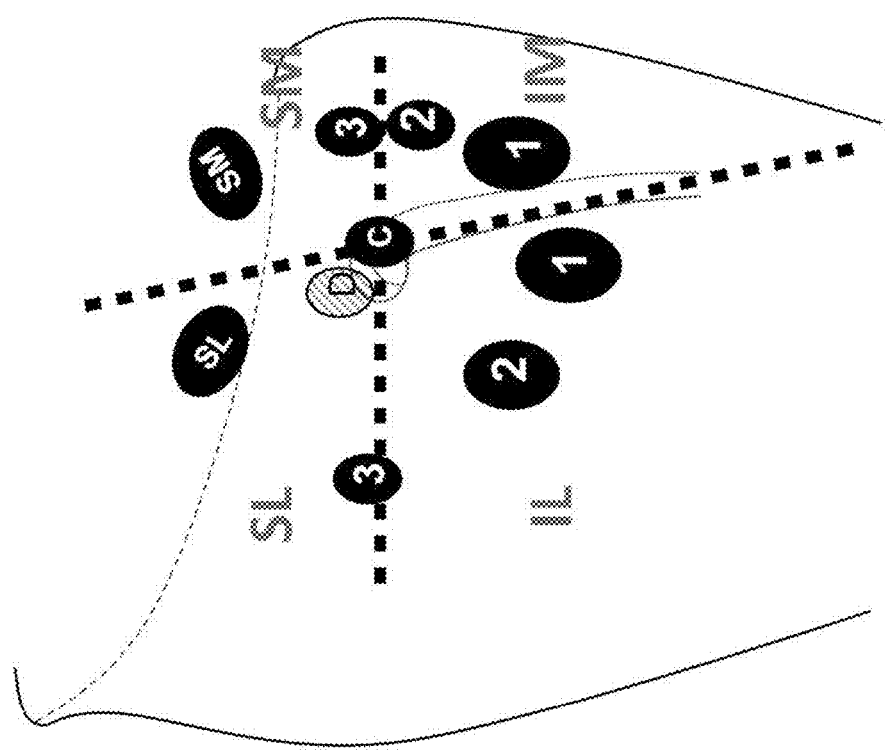
Fig.19

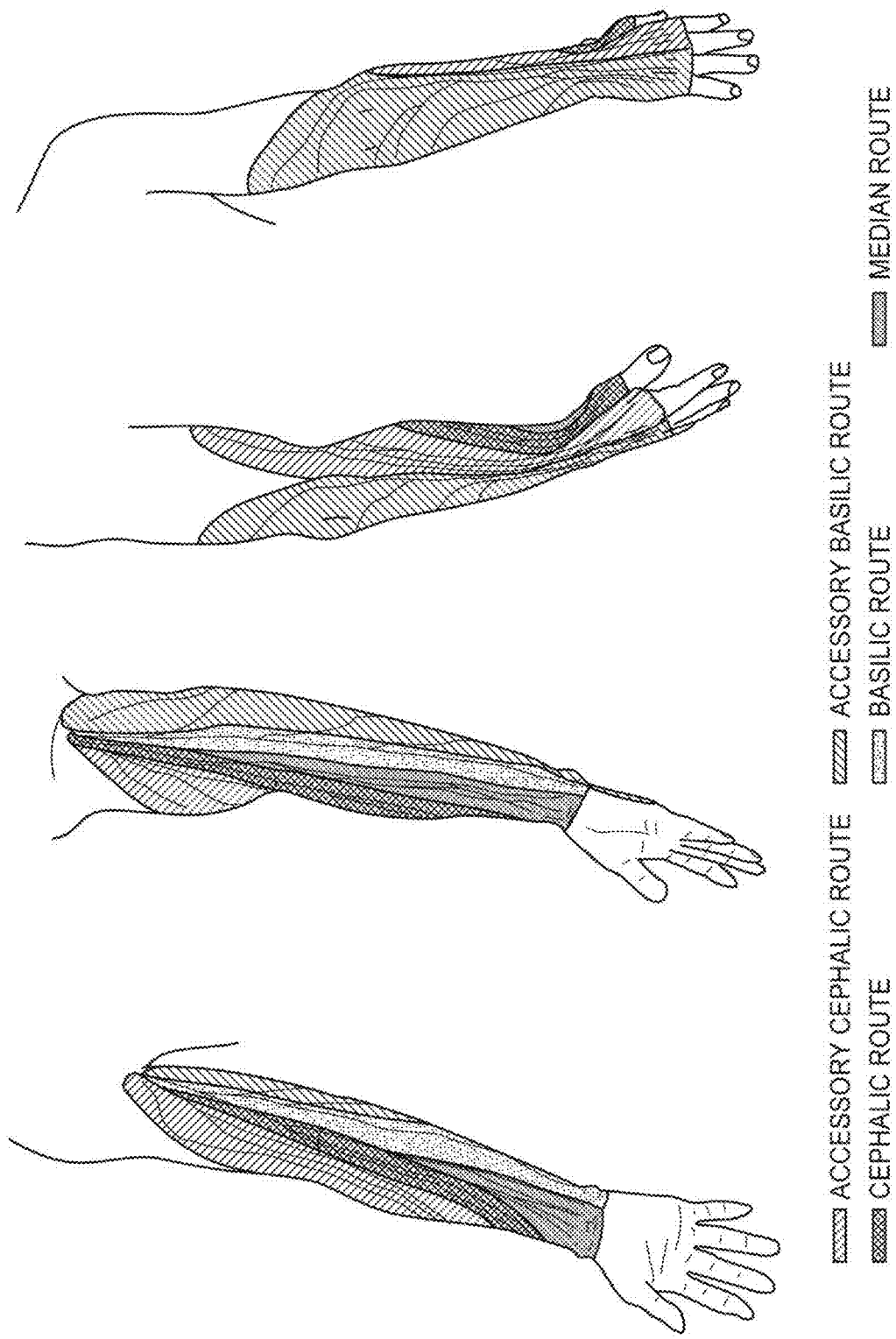

METHOD OF EVALUATING LYMPHATIC SYSTEM FUNCTION

TECHNICAL FIELD

Embodiments relate to a method of evaluating a lymphatic system function.

BACKGROUND

A lymphatic system is a network that functions as a circulatory system of lymph which includes lymph nodes, lymphatic vessels, other lymphatic tissues and the like. As a method of diagnosing diseases of a lymphatic system (for example, lymphedema) or the like, lymphography examination methods such as a method of injecting a fluorescent dye such as indocyanine green and imaging a lymphatic vessel by fluorescence observation or the like and a method of injecting a radioisotope such as $^{99m}$Tc-labeled tin colloid and visualizing the injected radioisotope by a scintigraphy have been known (for example, Non-Patent Literature 1 and Non-Patent Literature 2).

Non-Patent Literature 1: Unno N, Inuzuka K, Suzuki M, Yamamoto N, Sagara D, Nishiyama M, Konno H. Preliminary experience with a novel fluorescence lymphography using indocyanine green in patients with secondary lymphedema. J. Vasc. Surg. 2007; 45(5): 1016-1021.

Non-Patent Literature 2: Maegawa J, Mikami T, Yamamoto Y, Satake T, Kobayashi S. Types of lymphoscintigraphy and indications for lymphaticovenous anastomosis. Microsurgery. 2010 September; 30(6): 437-442.

SUMMARY

The lymphography examination is an indispensable examination for diagnosis of lymphedema, but has a fundamental problem stemming from anatomical problems. The lymphatic vessel originates from a blind end and the number of lymphatic vessels is incalculable, so that there are countless candidate sites into which a contrast medium is injected. In addition, there have been no reports on the relationship between a beginning part of the lymphatic system and the lymphatic vessel-lymph node (lymphatic route, lymphatic group, lymphatic bundle, or lymphatic pathway) connected thereto. That is, there is no information that can explain the relationship between the sites into which the contrast medium is injected and the lymphatic route to be imaged by taking in the contrast medium correspondingly. Therefore, none of the lymphography examinations which have already been performed can determine the injection sites with anatomical evidence. This has led to the development of inspection protocols for various injection sites.

In fact, in the case of lower limbs, there are many cases in which the contrast medium is injected only into a first interdigital part aiming at an anteromedial bundle accompanying a great saphenous vein, but there are cases in which the contrast medium is injected into other sites or multiple points. It is not considered whether it is possible to compare the examination results in the same way although the injection sites are different. In addition, although there are cases where the contrast medium is injected near a heel targeting a posterolateral bundle accompanying a small saphenous vein, there is no information on a beginning part corresponding thereto and the injection site determined to be able to reliably image the posterolateral bundle is not known. Even in the case of upper limbs, there is no fixed information similar to that described above.

The absence of the unified and complete examination protocol for imaging the lymphatic system means that there are no materials to commonly determine these effects for treatment policies as well as at the time of diagnosis.

The present inventors succeeded in mapping the anatomical information necessary for determining the injection site during the lymphography examination of the lower and upper limbs to details of the lymphatic route which can be imaged based the anatomical information. Based on the information, the present inventors clarified the relationship between an appropriate injection site for performing lymphography and a lymphatic route which can be visualized at this site. The embodiment is based on these novel findings and aims to provide a method of evaluating a lymphatic system function using a lymphatic route map.

The embodiment relates to a method of evaluating a lymphatic system function including: selecting one or a plurality of lymphatic routes to be evaluated from a plurality of lymphatic routes existing in four limbs; determining an injection site of a visualization agent based on information on the selected lymphatic route and injection sites of peripheries of four limbs corresponding to the selected lymphatic route; injecting the visualization agent from the selected injection site; and visualizing the injected visualization agent and evaluating functions of the one or plurality of lymphatic routes to be evaluated.

The embodiment relates to an apparatus of evaluating a lymphatic system function including: a first acquisition means configured to acquire information on an injection site of a visualization agent in peripheries of four limbs of a subject; a second acquisition means configured to acquire a visualization agent image of the subject into which the visualization agent is injected; a color setting means configured to set different colors for each lymphatic route existing in the four limbs on the visualization agent image acquired by the second acquisition means, based on the information acquired by the first acquisition means and information on a plurality of lymphatic routes existing in the four limbs and injection sites of the peripheries of the four limbs corresponding thereto; and an output means configured to output the visualization agent image with colors by the color setting means.

The embodiment relates to a program of evaluating a lymphatic system function arranged to make a computer function as: a first acquisition means configured to acquire information on an injection site of a visualization agent in peripheries of four limbs of a subject; a second acquisition means configured to acquire a visualization agent image of the subject into which the visualization agent is injected; a color setting means configured to set different colors for each lymphatic route existing in the four limbs on the visualization agent image acquired by the second acquisition means, based on the information acquired by the first acquisition means and information on a plurality of lymphatic routes existing in the four limbs and injection sites of the peripheries of the four limbs corresponding thereto; and an output means configured to output the visualization agent image with colors by the color setting means.

The embodiment relates to a computer-readable storage medium storing a program of evaluating a lymphatic system function.

Figure 1:
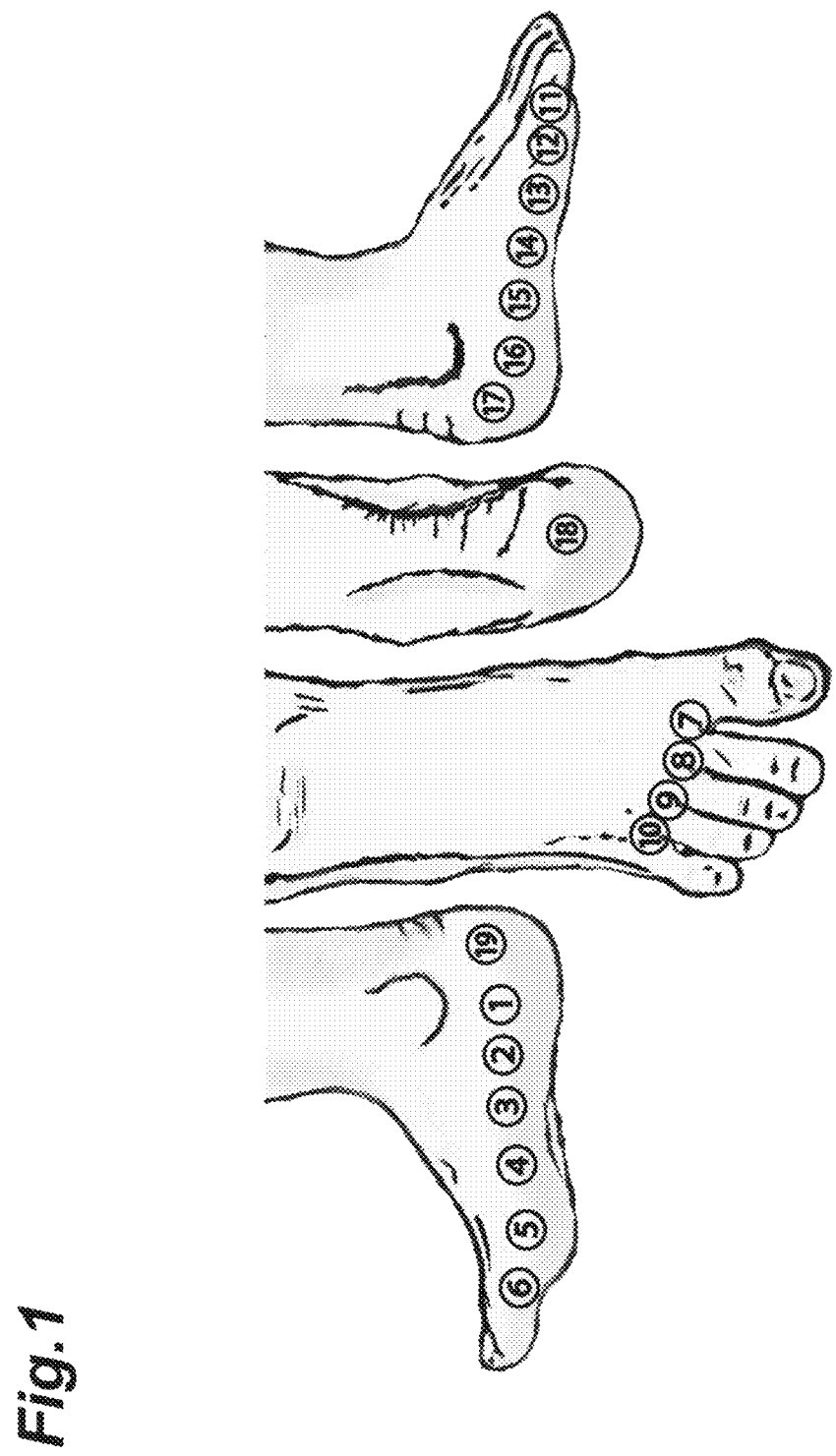
FIG. 1 is a schematic diagram of a periphery of a lower limb showing lower limb injection sites 1 to 19 of a contrast medium. Each lower limb injection site was set according to an anatomical landmark on a boundary line of dorsum pedis-planta pedis, and details thereof are as shown as follows.

Lower limb injection site 1: Below medial malleolus
Lower limb injection site 5: Head of first metatarsal bone
Lower limb injection site 6: Base of first proximal phalanx
Lower limb injection site 7: First interdigital part
Lower limb injection site 8: Second interdigital part
Lower limb injection site 9: Third interdigital part
Lower limb injection site 10: Fourth interdigital part
Lower limb injection site 11: Base of fifth proximal phalanx
Lower limb injection site 12: Head of fifth metatarsal bone
Lower limb injection site 16: Below lateral malleolus
Lower limb injection site 18: Calcaneal tuberosity
Lower limb injection site 3: Midpoint between lower limb injection site 1 and lower limb injection site 5
Lower limb injection site 2: Midpoint between lower limb injection site 1 and lower limb injection site 3
Lower limb injection site 4: Midpoint between lower limb injection site 3 and lower limb injection site 5
Lower limb injection site 14: Midpoint between lower limb injection site 12 and lower limb injection site 16
Lower limb injection site 13: Midpoint between lower limb injection site 12 and lower limb injection site 14
Lower limb injection site 15: Midpoint between lower limb injection site 14 and lower limb injection site 16
Lower limb injection site 17: Midpoint between lower limb injection site 16 and lower limb injection site 18
Lower limb injection site 19: Midpoint between lower limb injection site 18 and lower limb injection site 1

Figure 2:
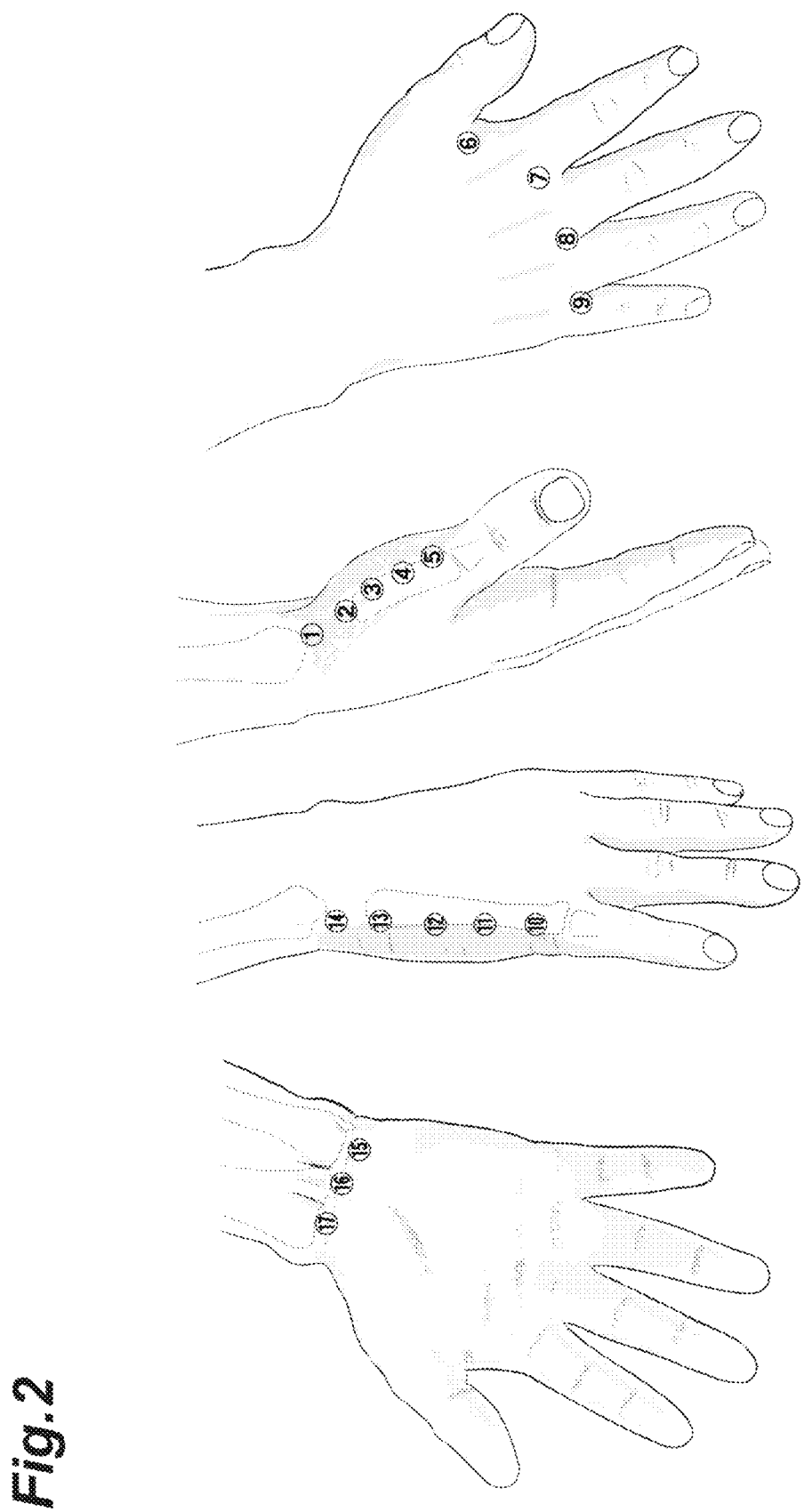

FIG. 2 is a schematic diagram of a periphery of an upper limb showing upper limb injection sites 1 to 17 of a contrast medium. Each upper limb injection site is set according to an anatomical landmark on a boundary of dorsum manus-palmar, and details thereof are shown as follows.

Upper limb injection site 1: Distal of radial styloid process
Upper limb injection site 5: The first head of metacarpal bone
Upper limb injection site 3: Midpoint between upper limb injection site 1 and upper limb injection site 5
Upper limb injection site 2: Midpoint between upper limb injection site 1 and upper limb injection site 3
Upper limb injection site 4: Midpoint between upper limb injection site 3 and upper limb injection site 5
Upper limb injection site 6: The first interdigital space
Upper limb injection site 7: The second interdigital space
Upper limb injection site 8: The third interdigital space
Upper limb injection site 9: The fourth interdigital space
Upper limb injection site 10: The fifth head of metacarpal bone
Upper limb injection site 14: Distal of radial styloid process
Upper limb injection site 12: Midpoint between upper limb injection site 10 and upper limb injection site 14
Upper limb injection site 11: Midpoint between upper limb injection site 10 and upper limb injection site 12
Upper limb injection site 13: Midpoint between upper limb injection site 12 and upper limb injection site 14
Upper limb injection site 16: Midpoint between upper limb injection site 1 and upper limb injection site 14 (palmar side)
Upper limb injection site 15: Midpoint between upper limb injection site 14 and upper limb injection site 16
Upper limb injection site 17: Midpoint between upper limb injection site 16 and upper limb injection site 1

Figure 3:
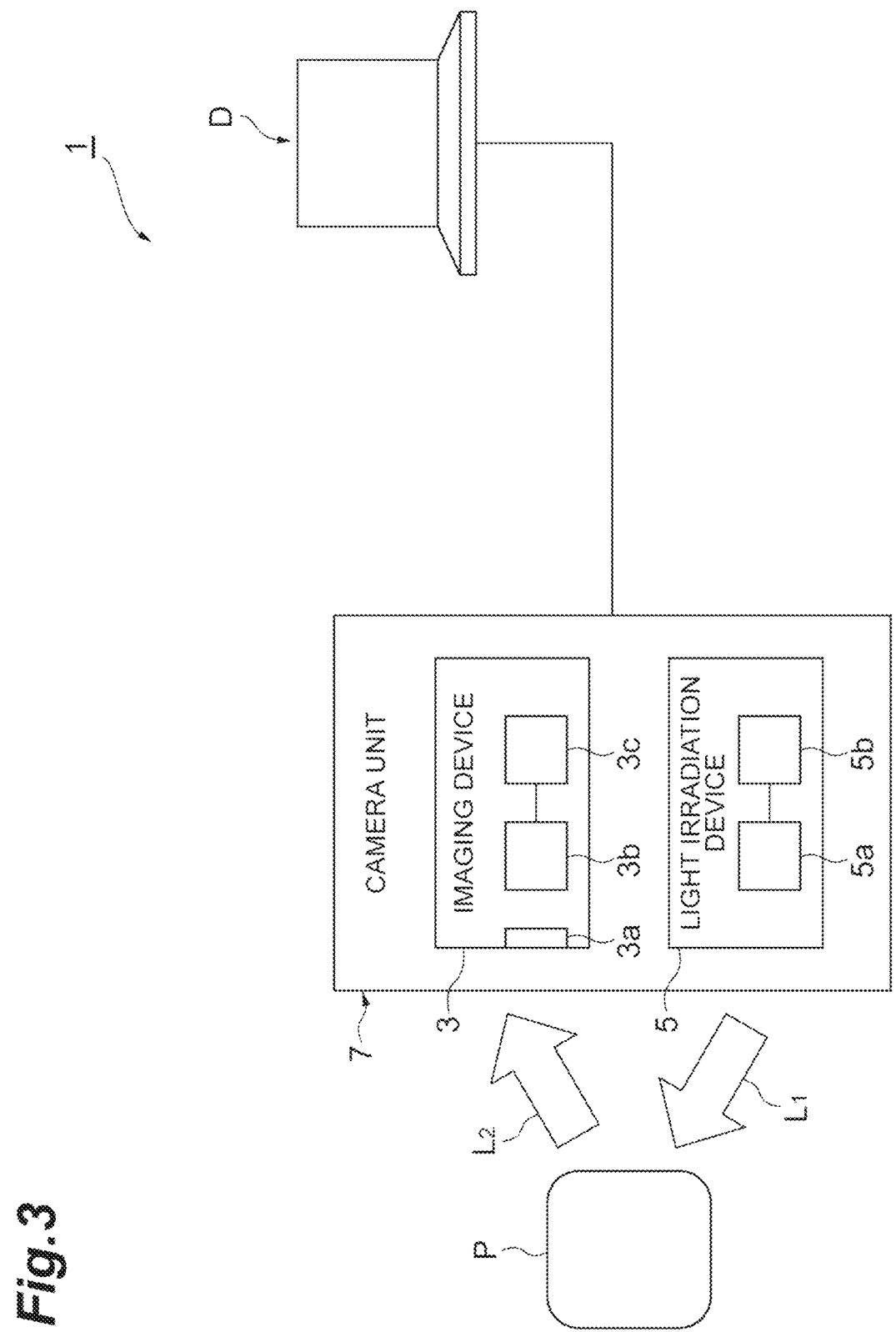

FIG. 3 is a block diagram showing a schematic configuration of a system of evaluating a lymphatic system function according to an embodiment.

Figure 4:
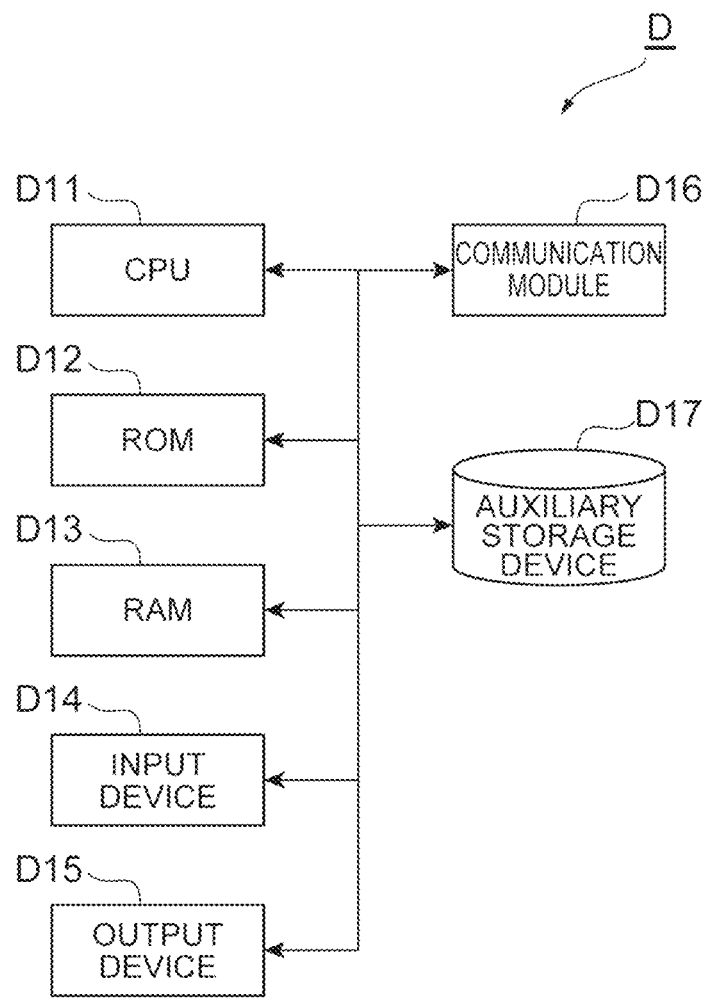

FIG. 4 is a schematic diagram showing a hardware configuration of an apparatus of evaluating a lymphatic system function according to an embodiment.

Figure 5:
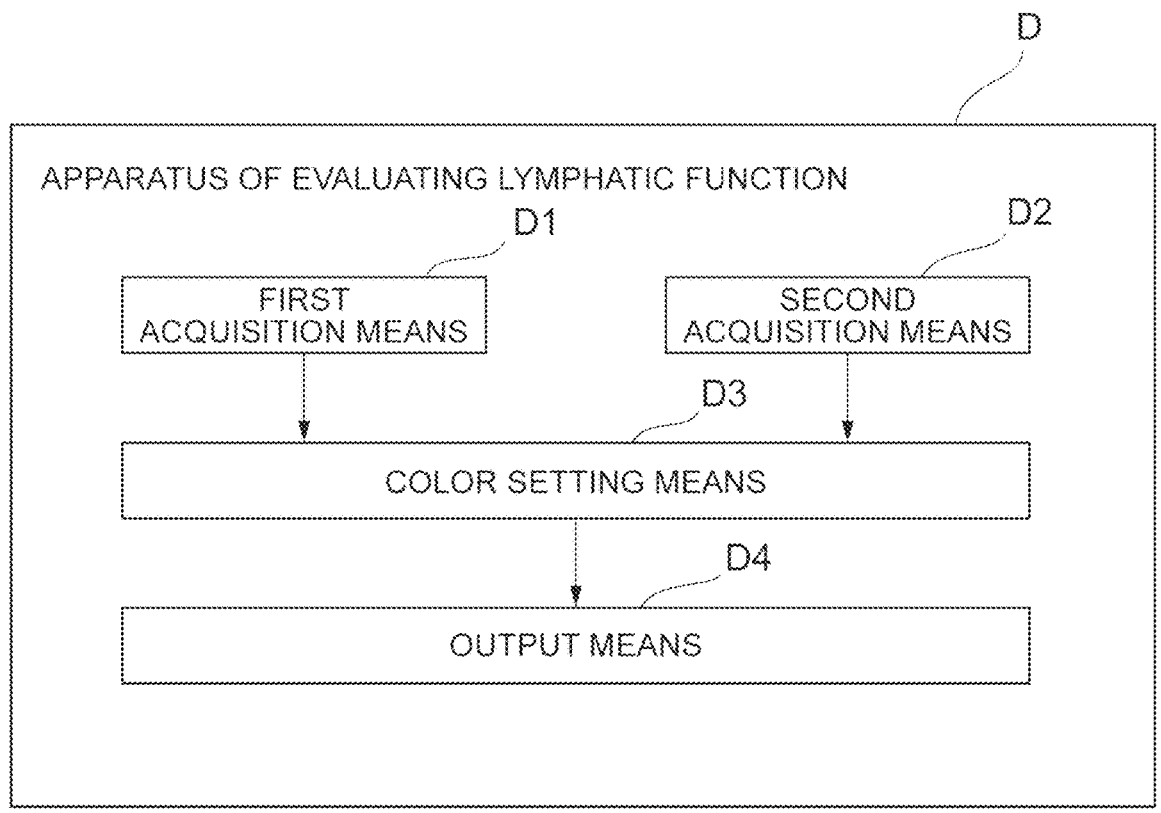

FIG. 5 is a schematic diagram showing a functional configuration of the apparatus of evaluating a lymphatic system function according to an embodiment.

Figure 6A:
Figure 6B:
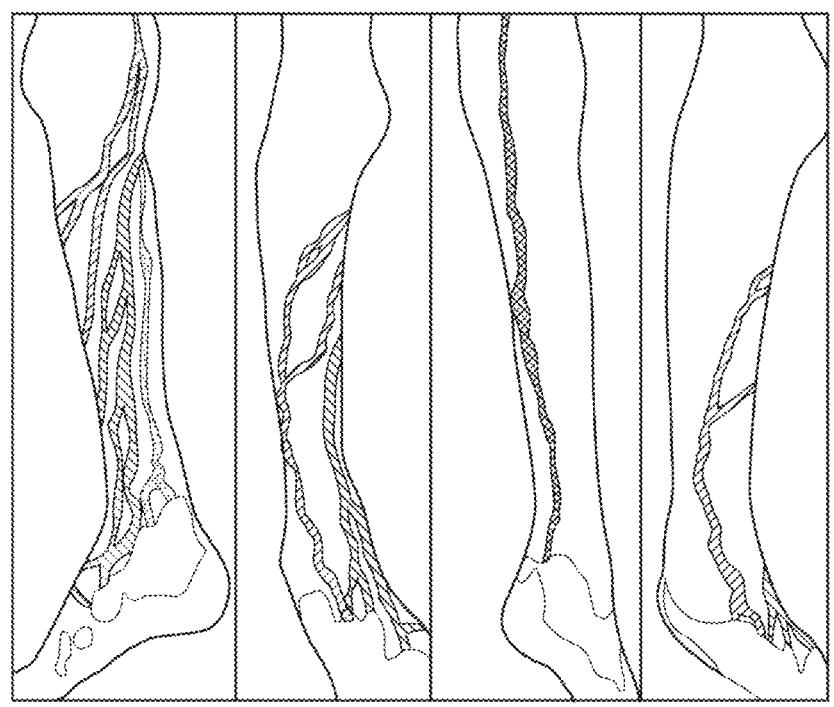

FIG. 6A is a photograph showing an example of a lymphangiography examination result of a lower limb. "x" indicates posterior edge of lateral malleolus. "A" indicates anterior edge of medial malleolus. "O" indicates calcaneal tuberosity. "□" indicates an anterior midpoint between the anterior edge of the medial malleolus and the posterior edge of the lateral malleolus. A heel side using "x" and "Δ" as the boundary is "posterior", and an opposite side thereto is "anterior". "Medial" and "lateral" are defined based on the calcaneal tuberosity (indicated by "O") and the anterior midpoint (indicated by "□") between the anterior edge of the medial malleolus and the posterior edge of the lateral malleolus. Based on "O" and "□" as the boundary, the medial malleolus side is "medial", and the lateral malleolus side is "lateral". FIG. 6B is a trace diagram of FIG. 6A.

Figure 7A:
Figure 7B:
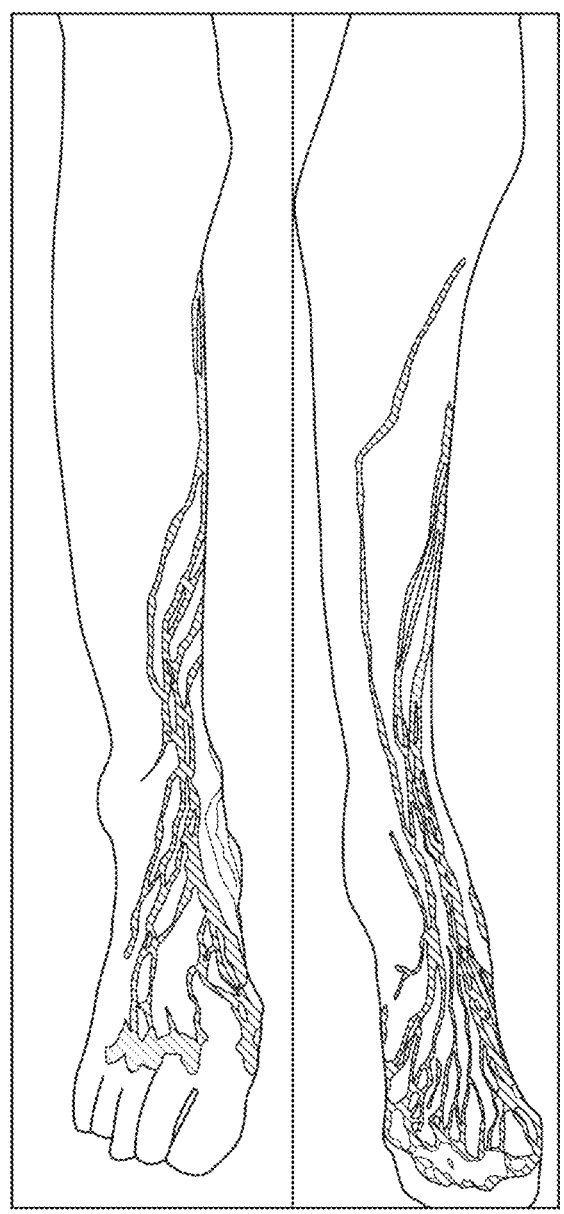

FIG. 7A is a photograph showing an example of results obtained by imaging the anteromedial route of the lower limb. "□" indicates the anterior midpoint between the anterior edge of the medial malleolus and the posterior edge of the lateral malleolus. "◇" indicates a midpoint between "□" and tibial tuberosity. FIG. 7B is a trace diagram of FIG. 7A.

Figure 8A:
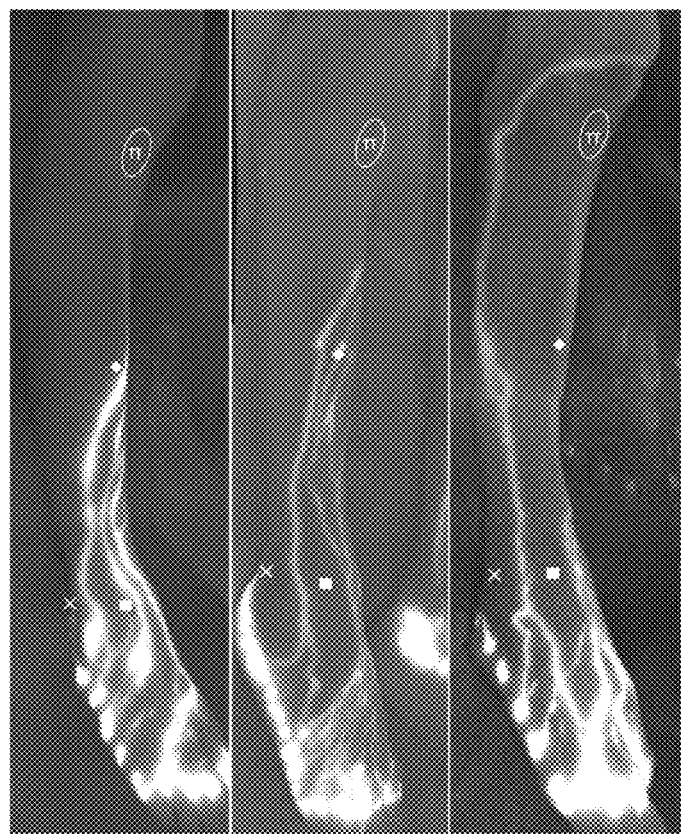
Figure 8B:

FIG. 8A is a photograph showing an example of results obtained by imaging the anterolateral route of the lower limb. "x" indicates the posterior edge of the lateral malleolus. "□" indicates the anterior midpoint between the anterior edge of the medial malleolus and the posterior edge of the lateral malleolus. "◇" indicates the midpoint between "□" and the tibial tuberosity. FIG. 8B is a trace diagram of FIG. 8A.

Figure 9A:
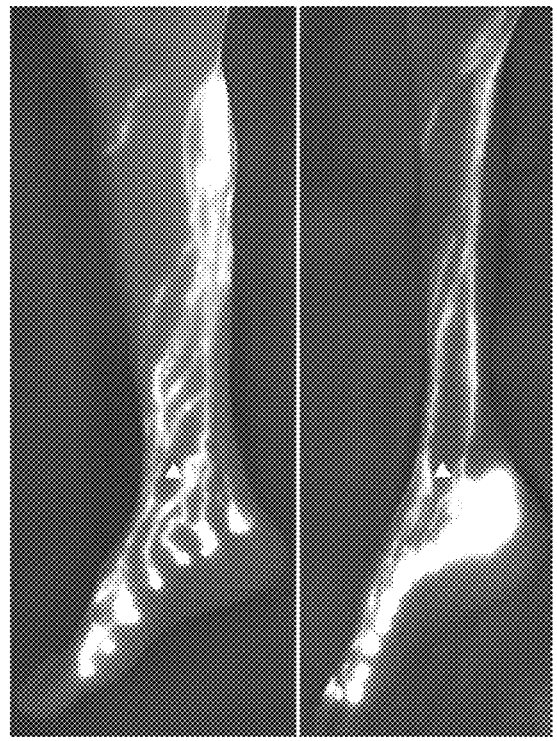
Figure 9B:
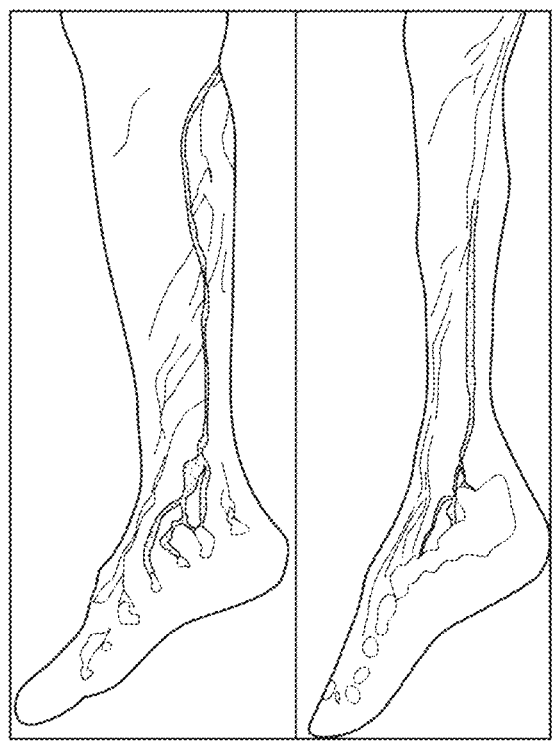

FIG. 9A is a photograph showing an example of results obtained by imaging the posteromedial route of the lower limb. "A" indicates the anterior edge of the medial malleolus. FIG. 9B is a trace diagram of FIG. 9A.

Figure 10:
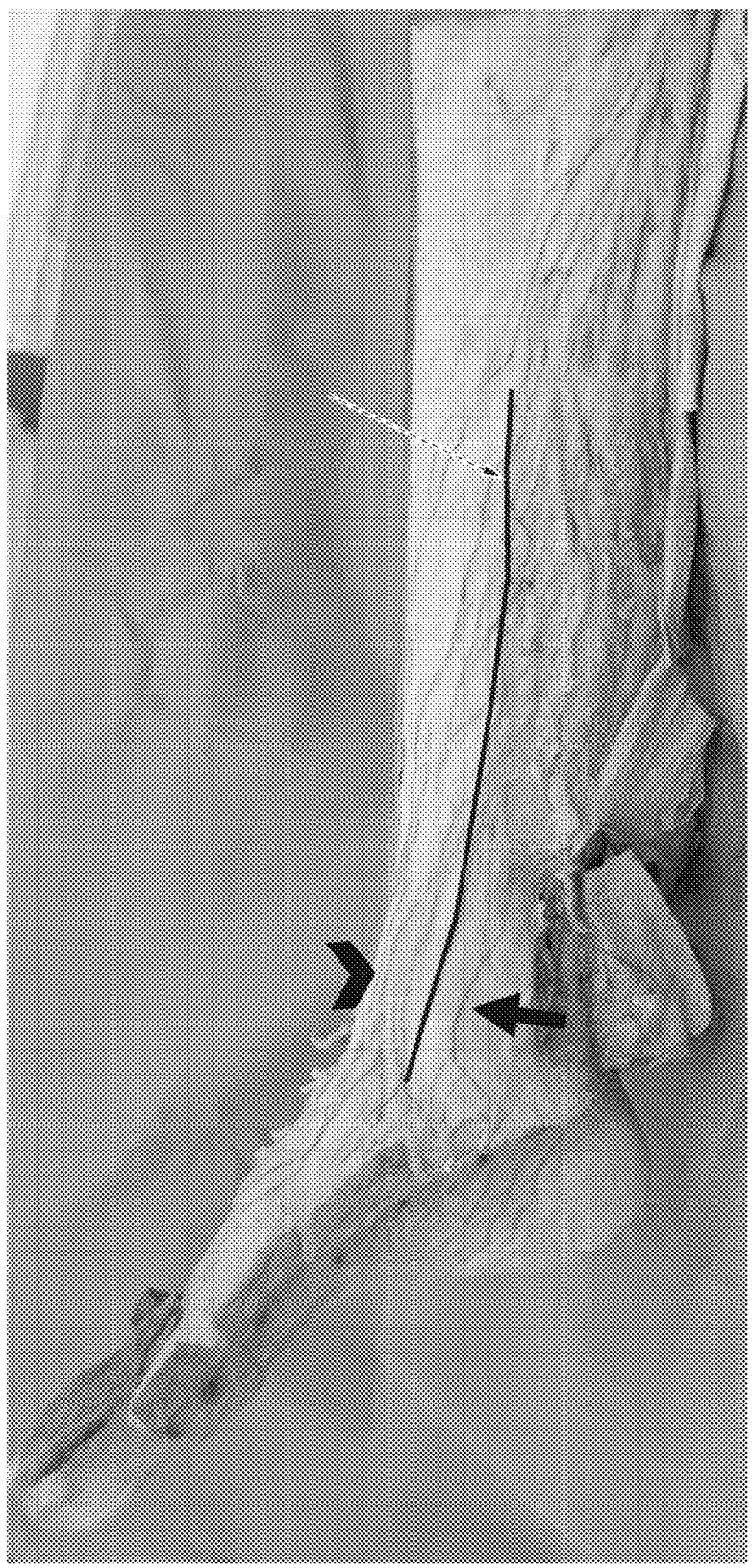

FIG. 10 is a photograph obtained by photographing a lymphatic vessel of a lower leg by injecting a dye into the lymphatic vessel and dissecting the lymphatic vessel.

Figure 11:
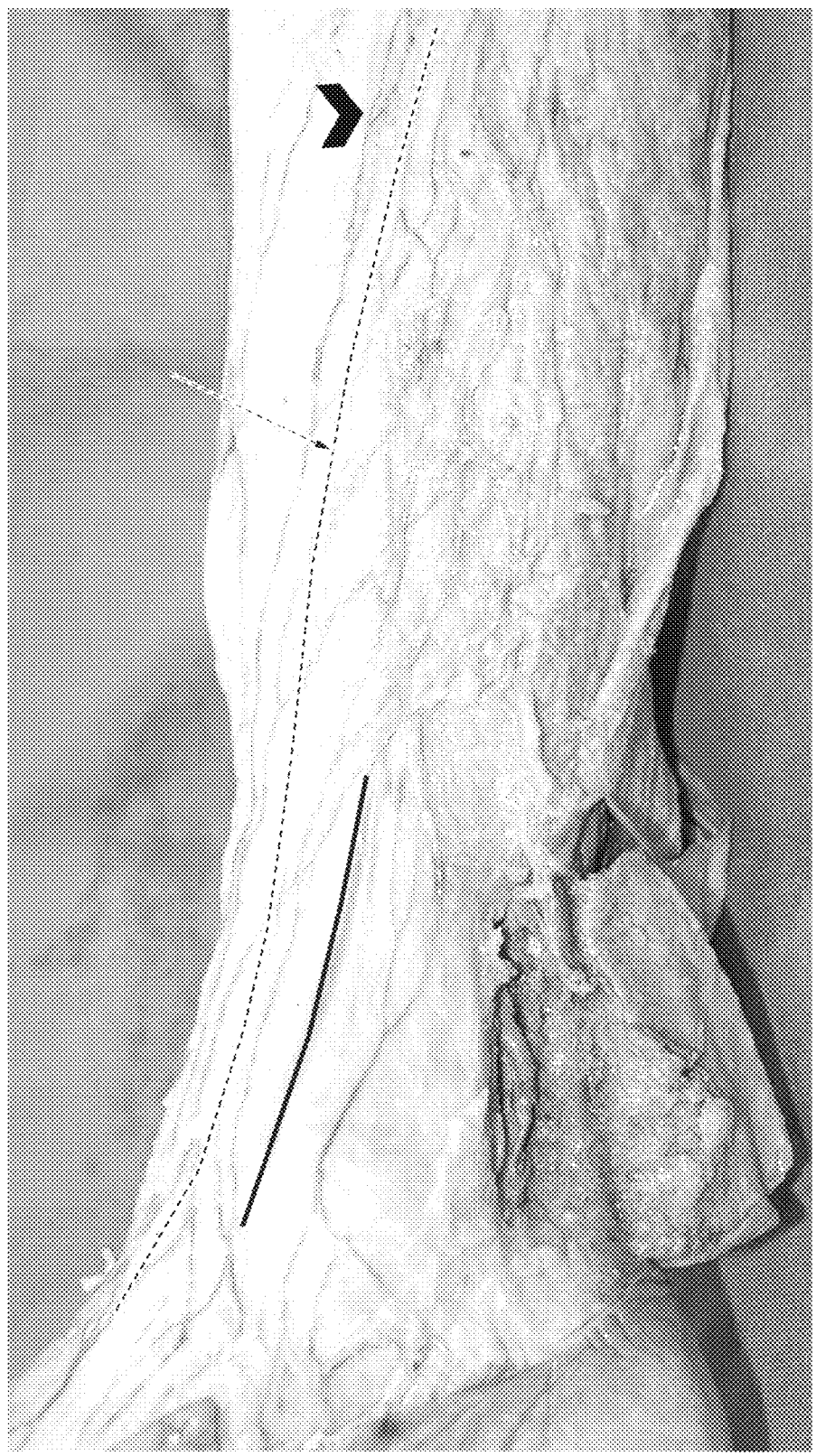

FIG. 11 is a photograph obtained by photographing the lymphatic vessel of the lower leg by injecting the dye into the lymphatic vessel and dissecting the lymphatic vessel.

Figure 12:
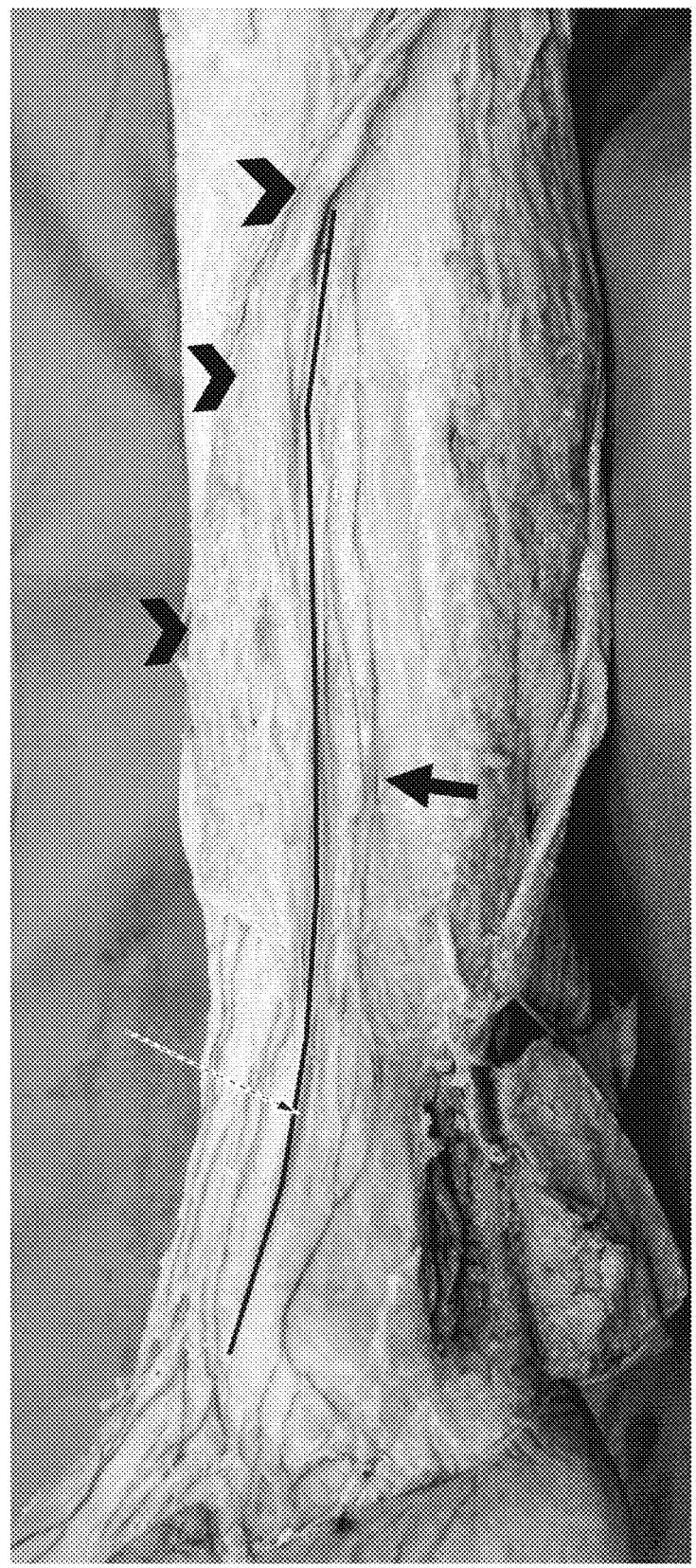

FIG. 12 is a photograph obtained by photographing the lymphatic vessel of the lower leg by injecting the dye into the lymphatic vessel and dissecting the lymphatic vessel.

Figure 13:

FIG. 13 is a photograph obtained by photographing the lymphatic vessel of the lower leg by injecting the dye into the lymphatic vessel and dissecting the lymphatic vessel.

Figure 14A:
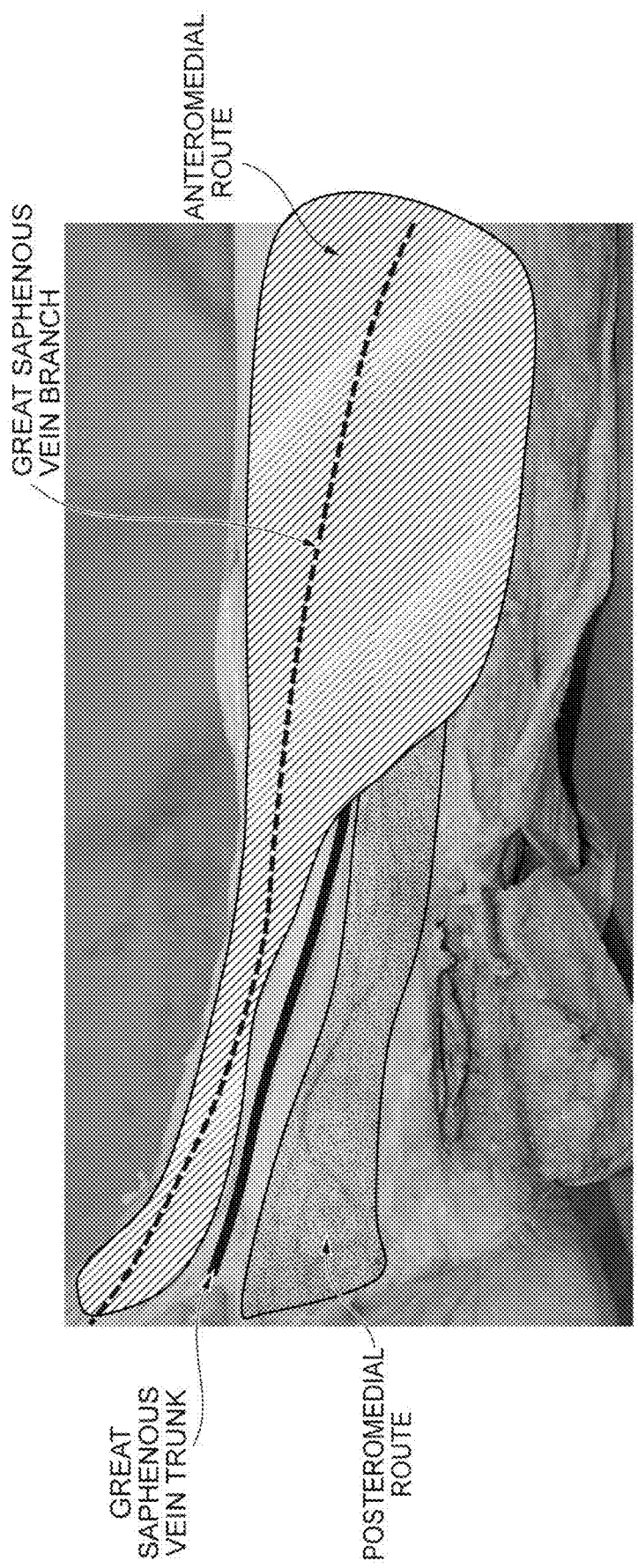
Figure 14B:
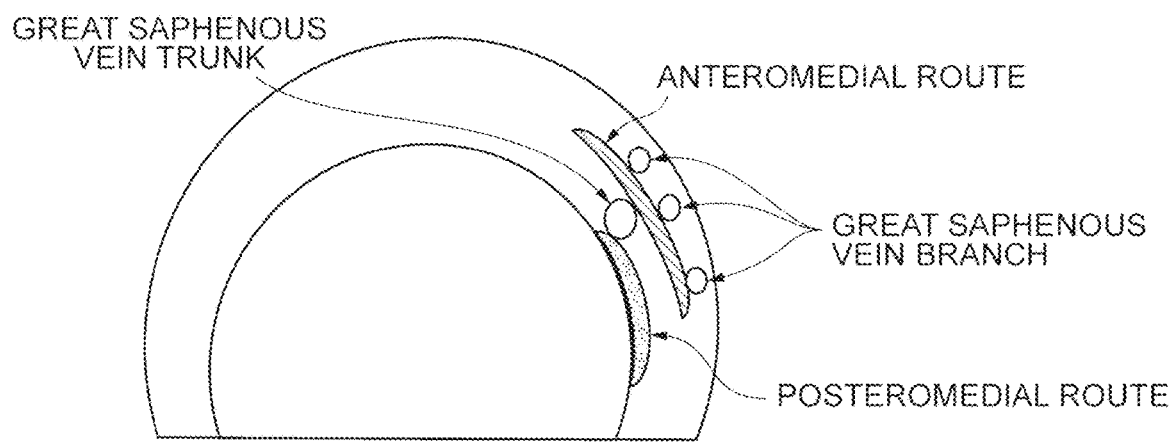

FIG. 14A and FIG. 14B are diagrams schematically showing the results of FIGS. 10 to 13.

Figure 15:
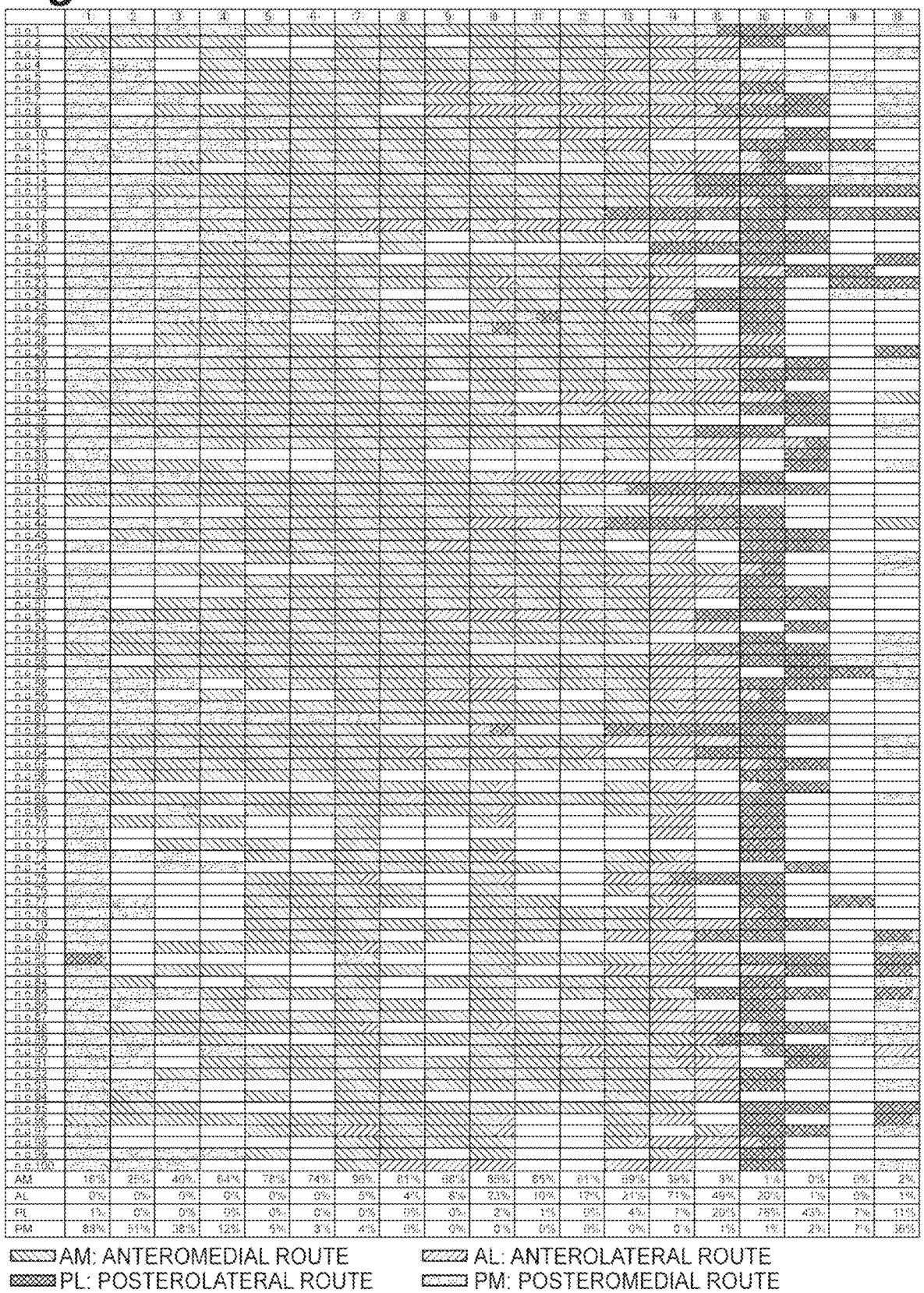

FIG. 15 is a table showing a mapping of the relationships between the lower limb injection sites 1 to 19 in each body donation and the lymphatic route (anteromedial route, posterolateral route, anterolateral route, or posteromedial route) of the lower limb corresponding to each lower limb injection site.

Figure 16:
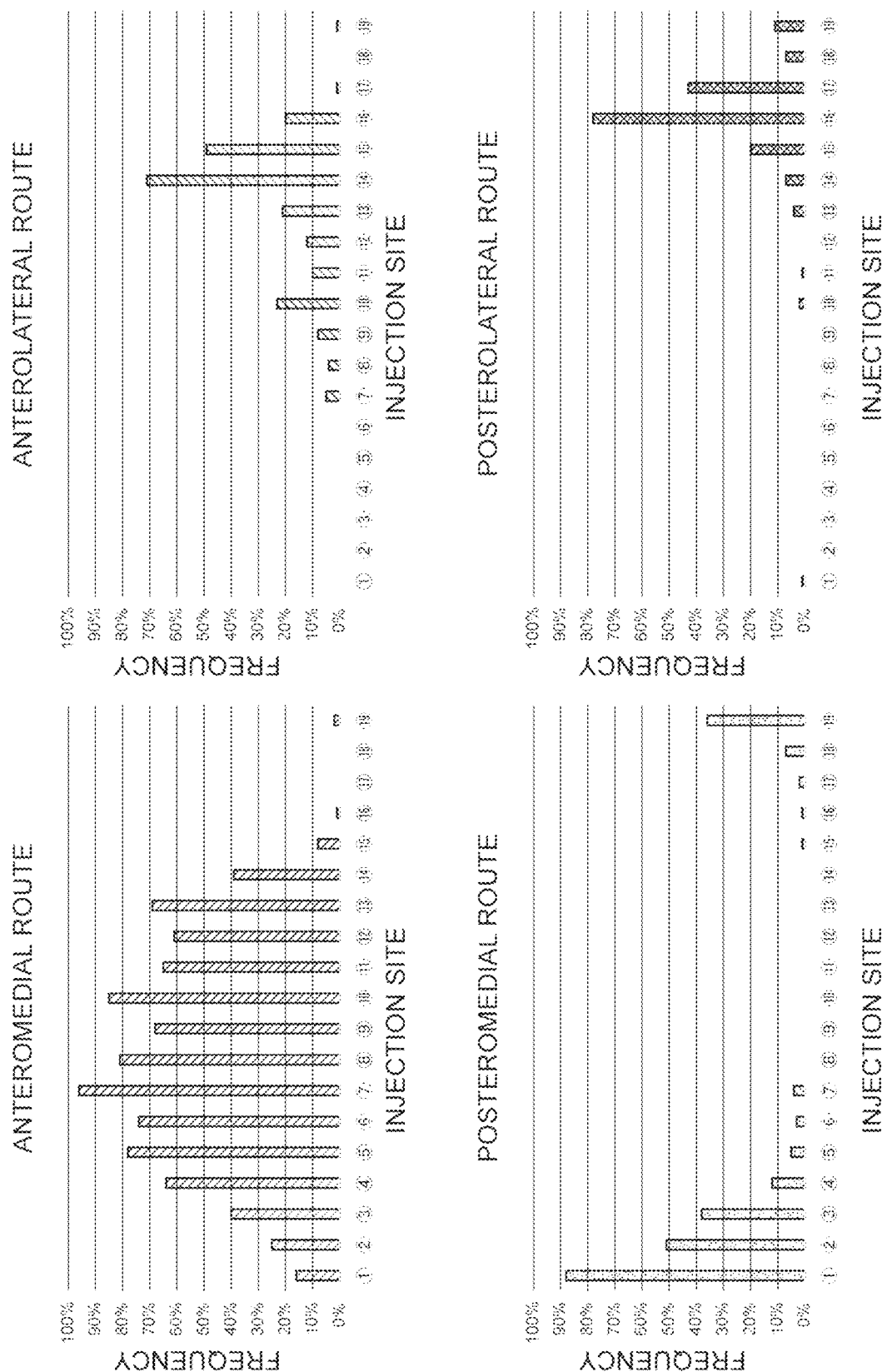

FIG. 16 is a graph showing a frequency at which imaging can be made for each lower limb injection site, for each lymphatic route (anteromedial route, posterolateral route, anterolateral route, or posteromedial route) of the lower limb.

Figure 17:
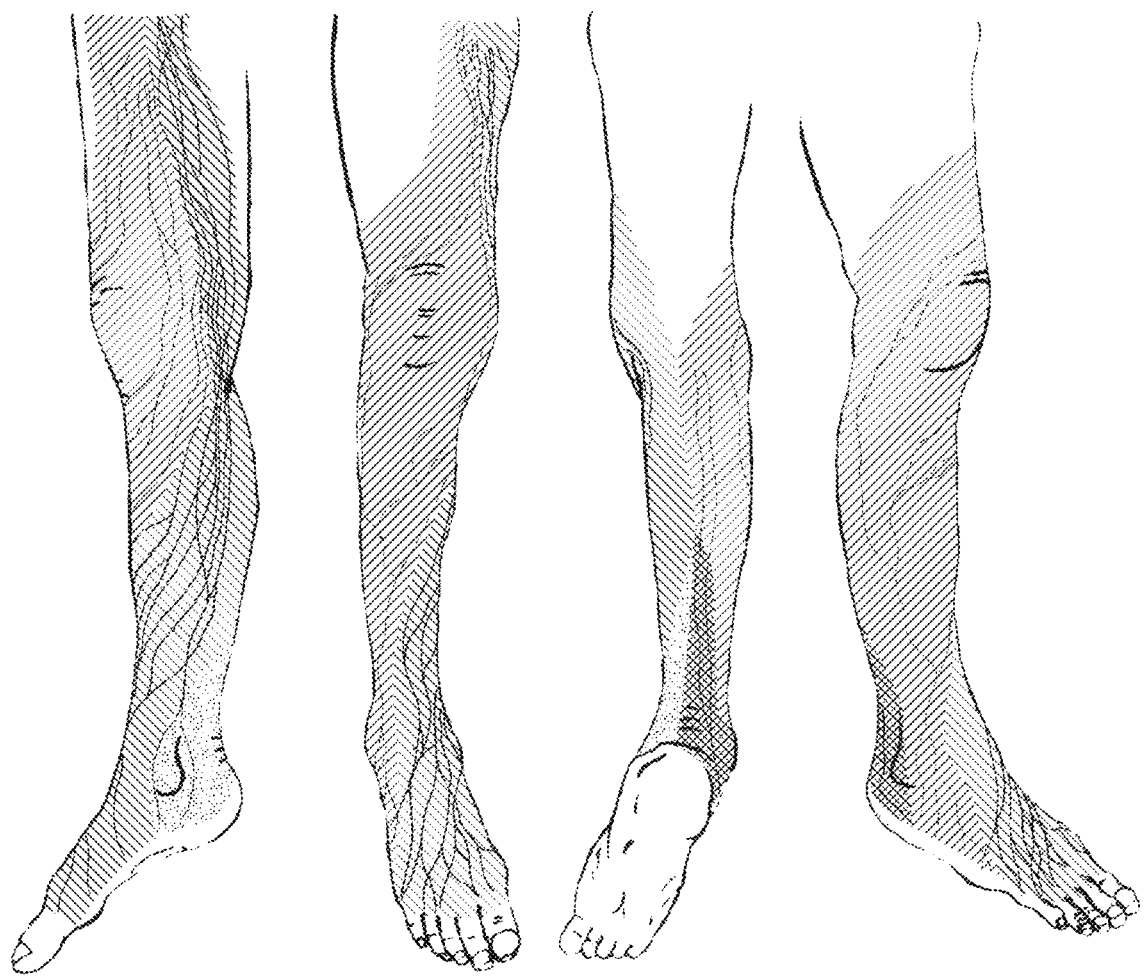

FIG. 17 is a schematic diagram showing a mapping of regions occupied by each lymphatic route (anteromedial route, posterolateral route, anterolateral route, or posteromedial route) of the lower limb below the lower limb.

Figure 18A:
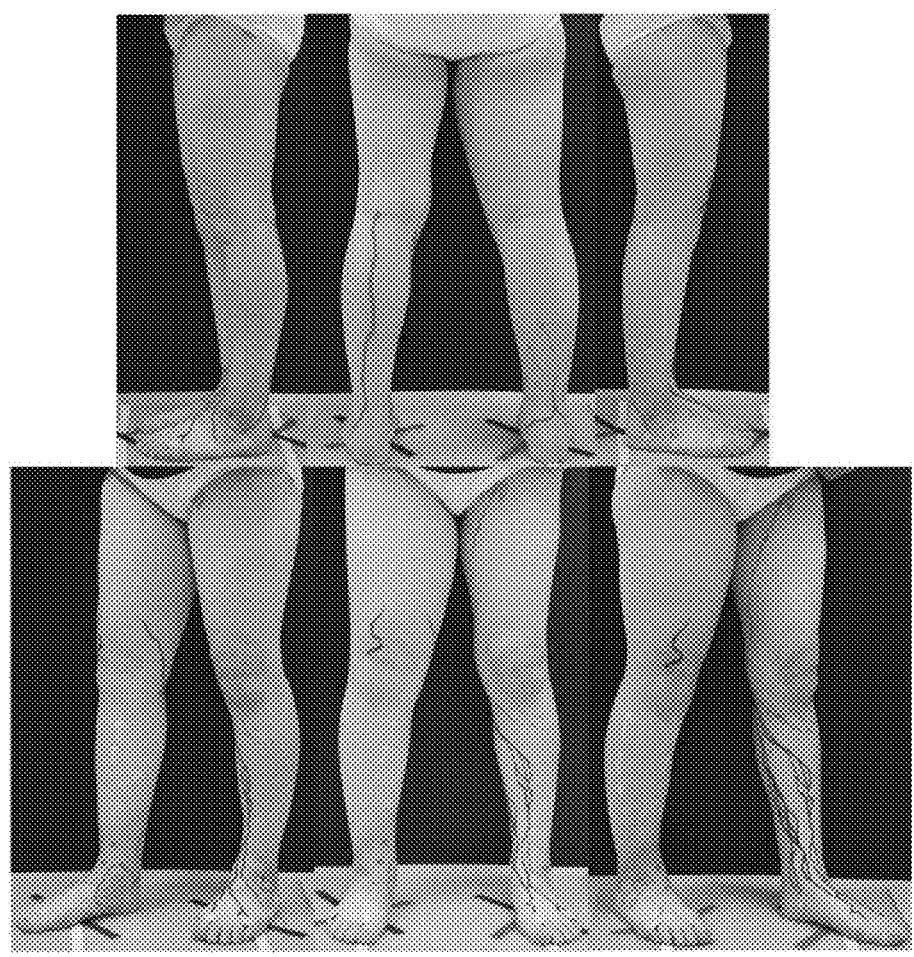
Figure 18B:

FIG. 18A is a photograph showing lower limbs of a patient whose lymphatic vessels are imaged by a method according to an embodiment. FIG. 18B is a trace diagram of FIG. 18A.

FIG. 19 is a diagram showing a definition of a superficial lymph node group at an inguinal region in this specification.

Figure 20:
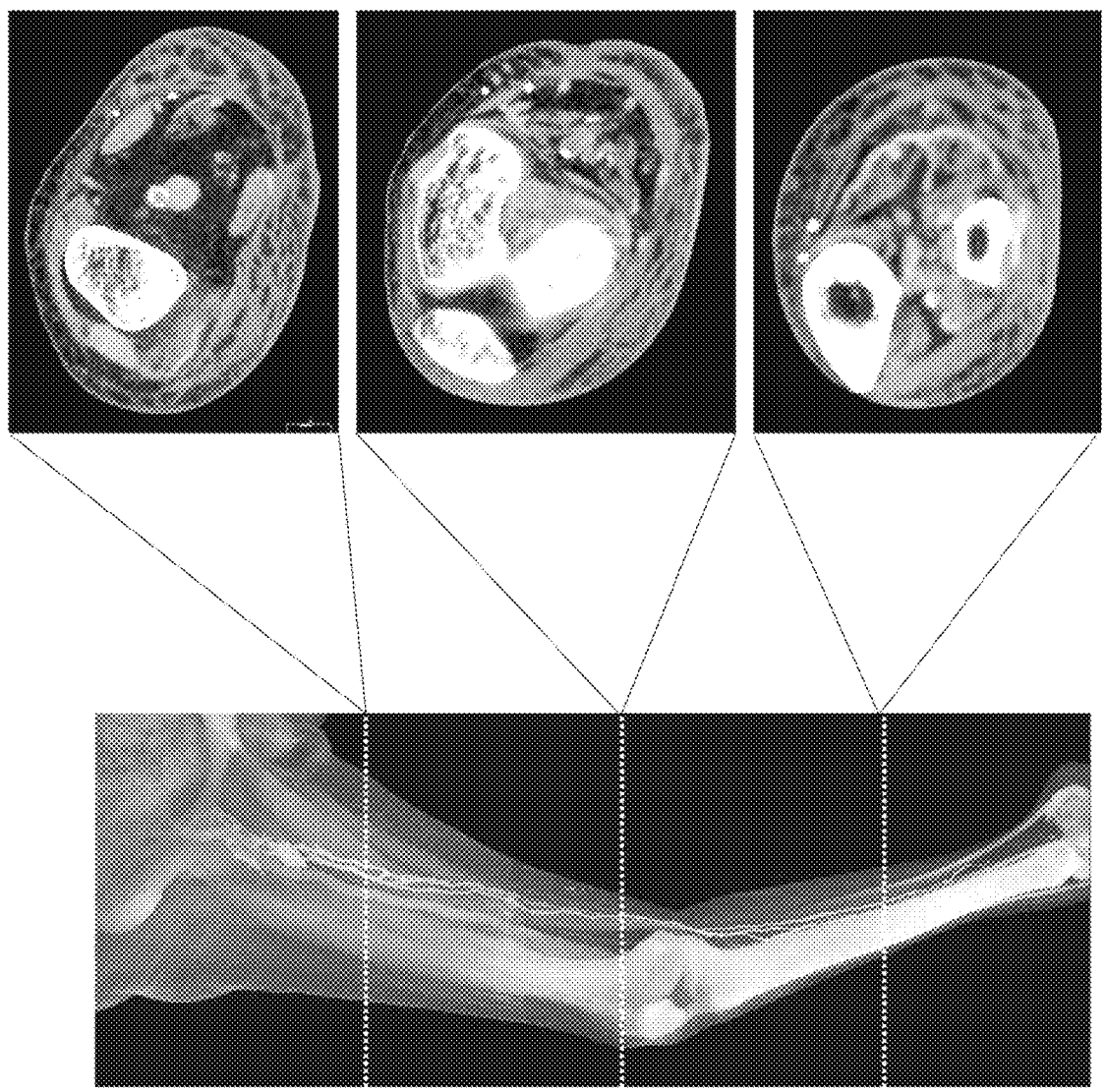

FIG. 20 is an image obtained by three-dimensionally constructing a CT lymphangiography image showing traveling of the lymphatic route upon imaging the posteromedial route.

Figure 21:
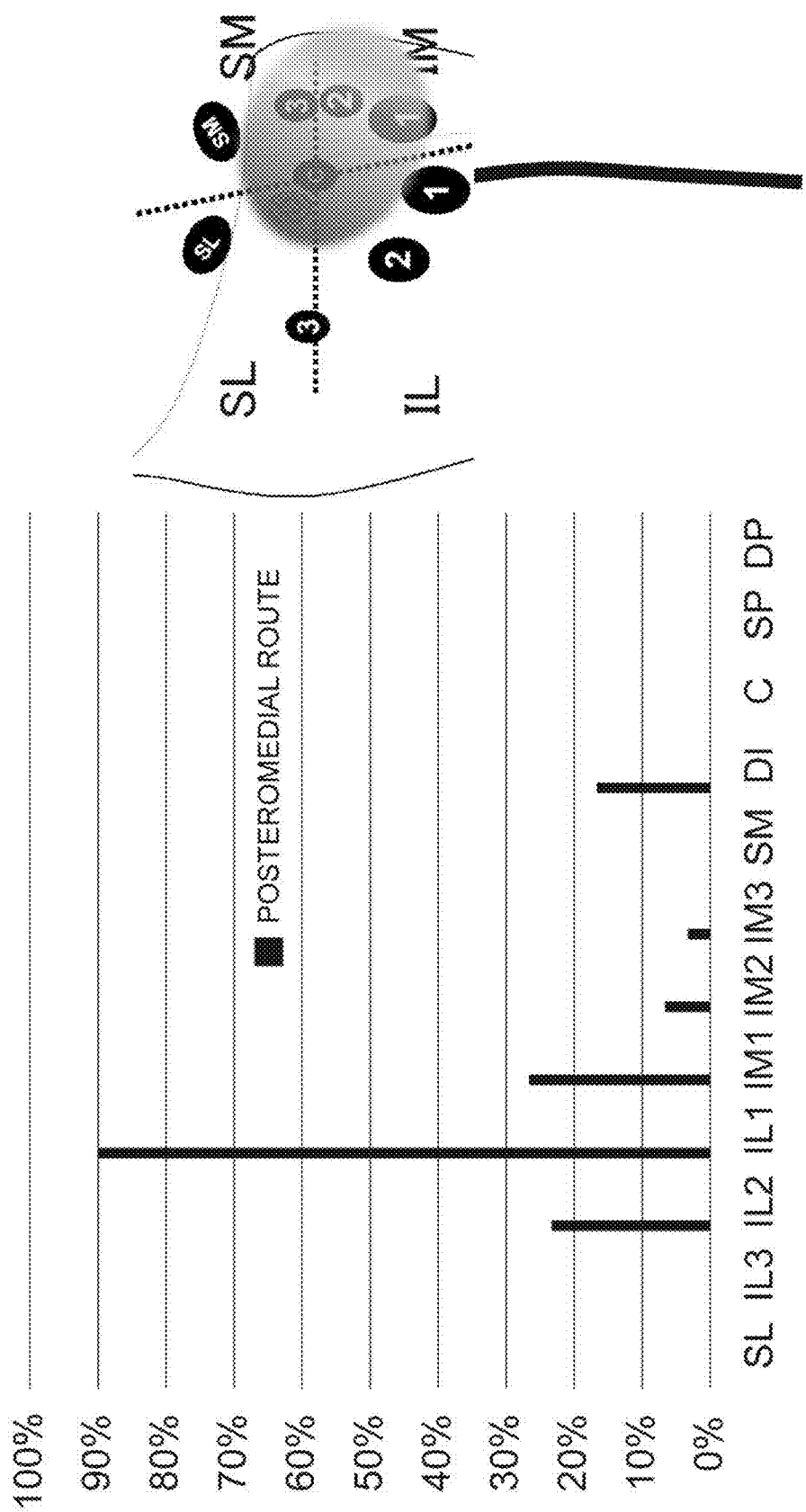

FIG. 21 is a graph plotting a frequency at which the posteromedial route reaches the first lymph nodes.

Figure 22:
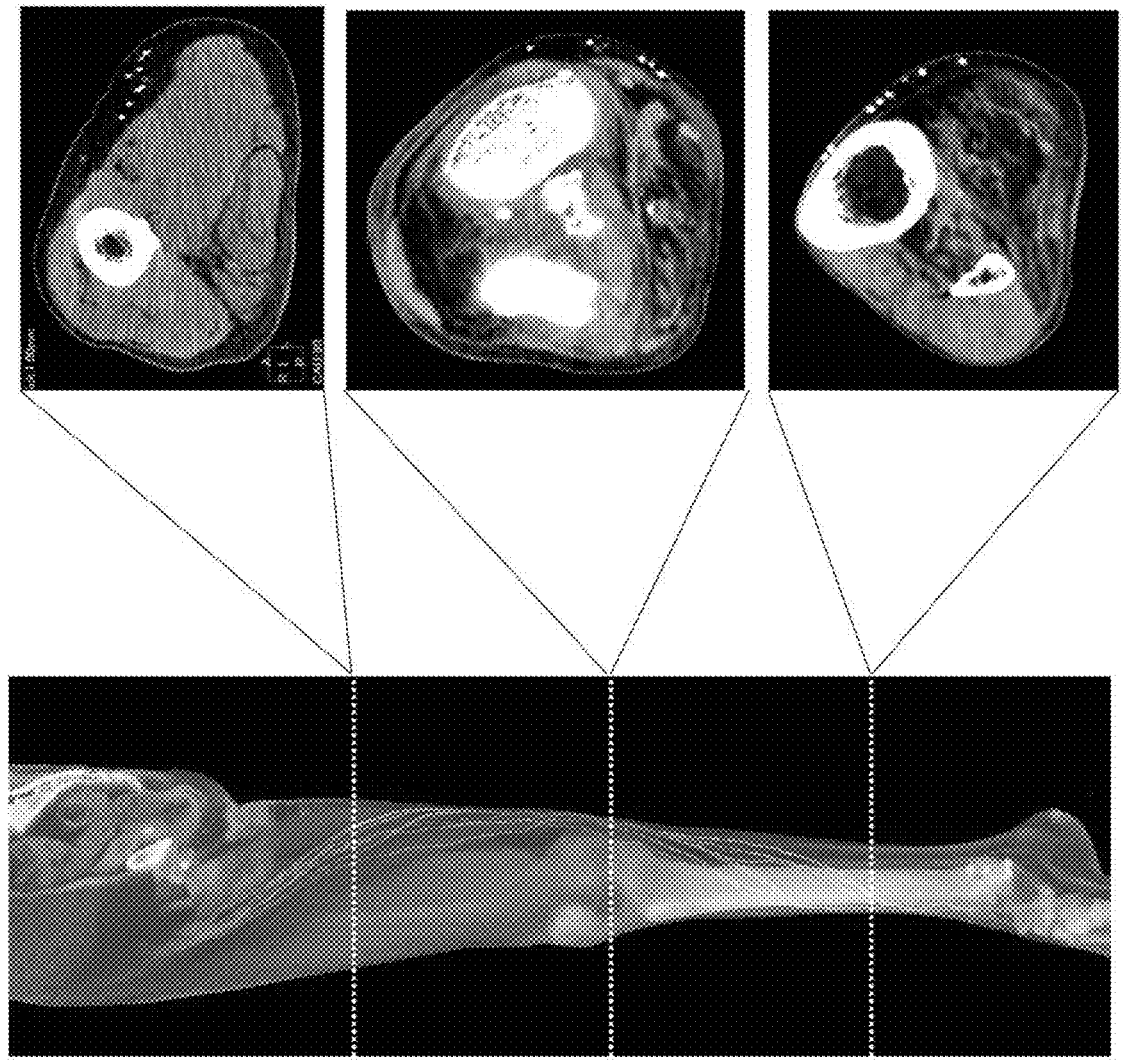

FIG. 22 is an image obtained by three-dimensionally constructing the CT lymphangiography image showing the traveling of the lymphatic route upon imaging the anteromedial route.

Figure 23:
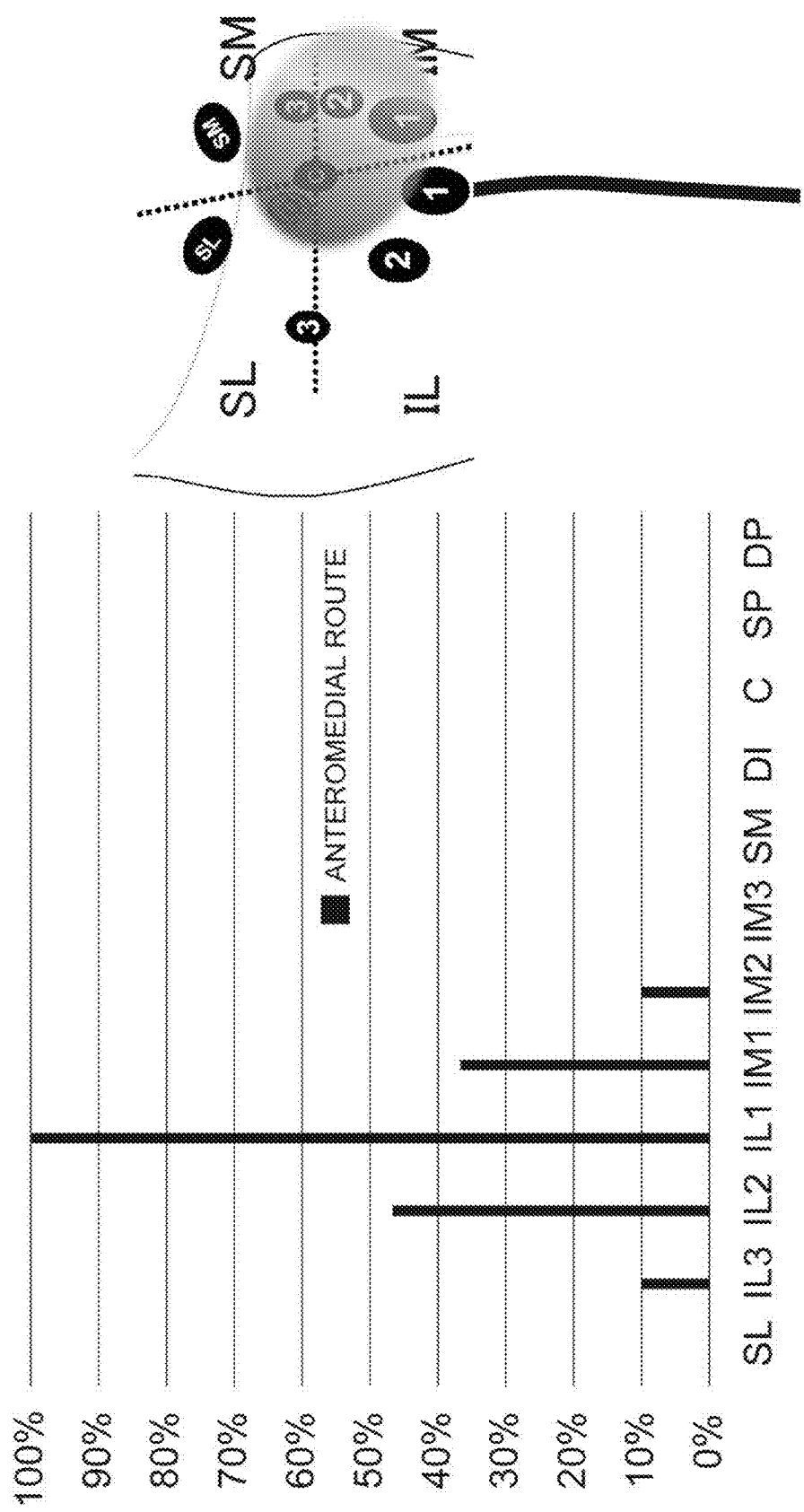

FIG. 23 is a graph plotting the frequency at which the anteromedial route reaches the first lymph nodes.

Figure 24:
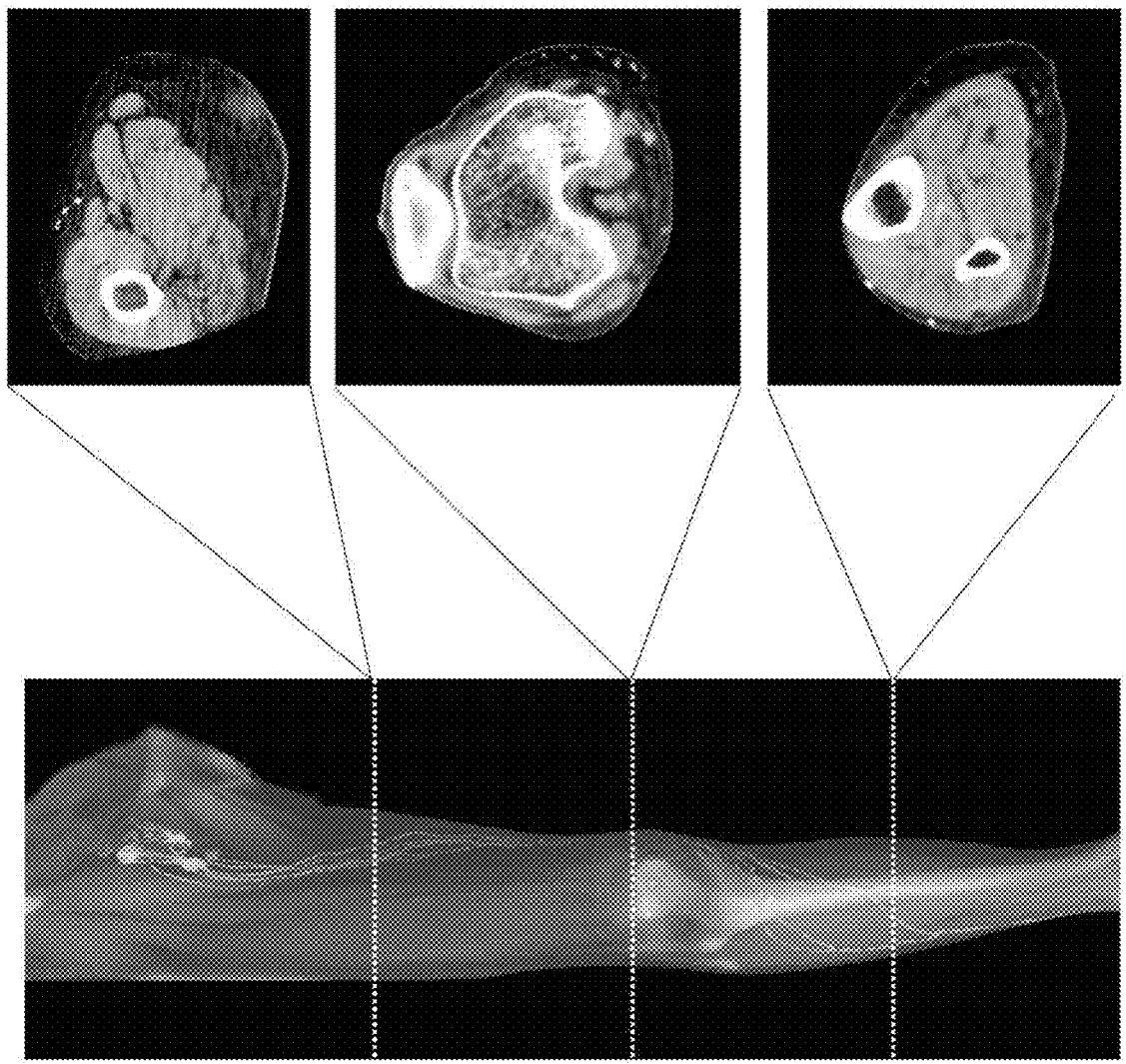

FIG. 24 is an image obtained by three-dimensionally constructing the CT lymphangiography image showing the traveling of the lymphatic route upon imaging the anterolateral route.

Figure 25:
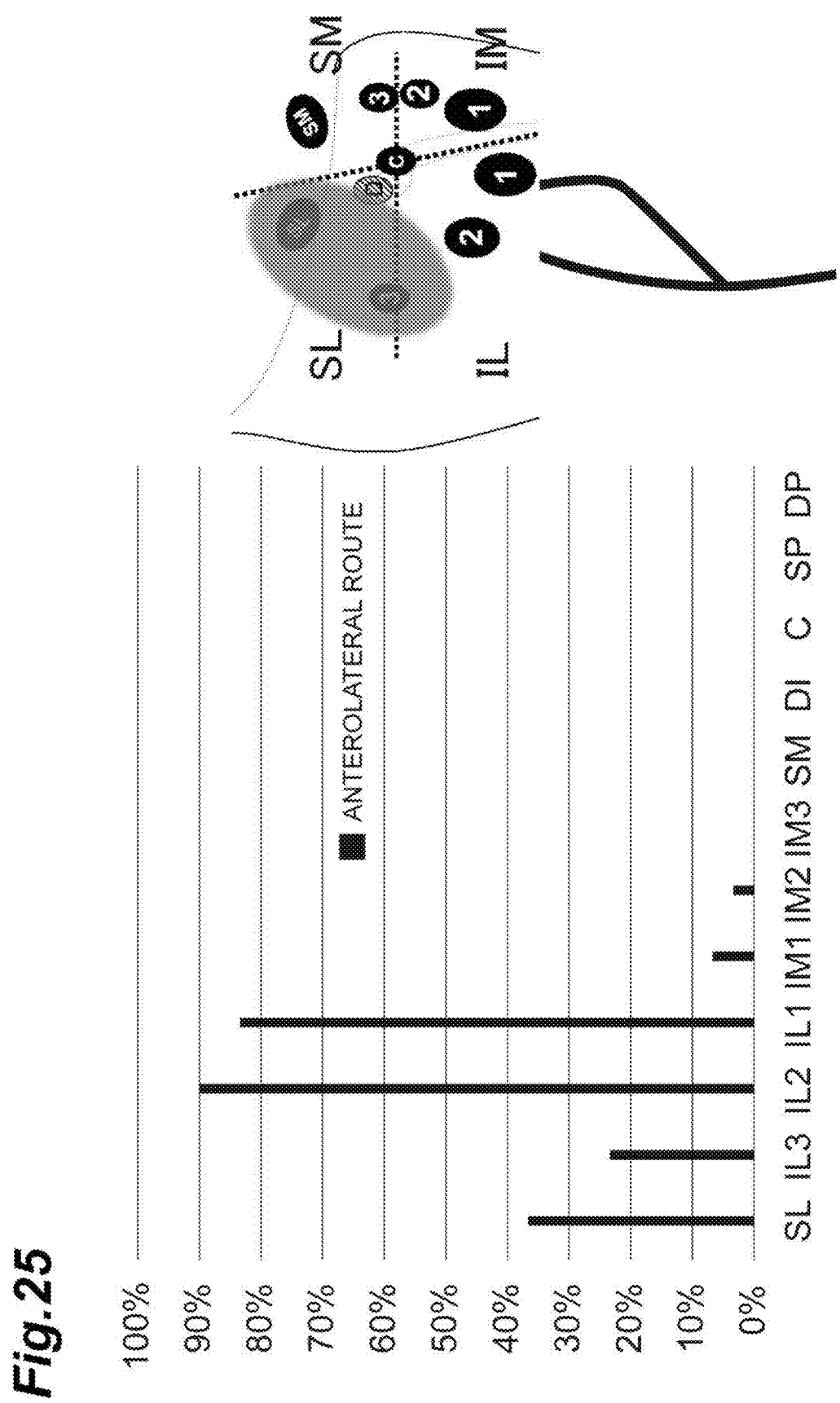

FIG. 25 is a graph plotting the frequency at which the anterolateral route reaches the first lymph nodes.

Figure 26:
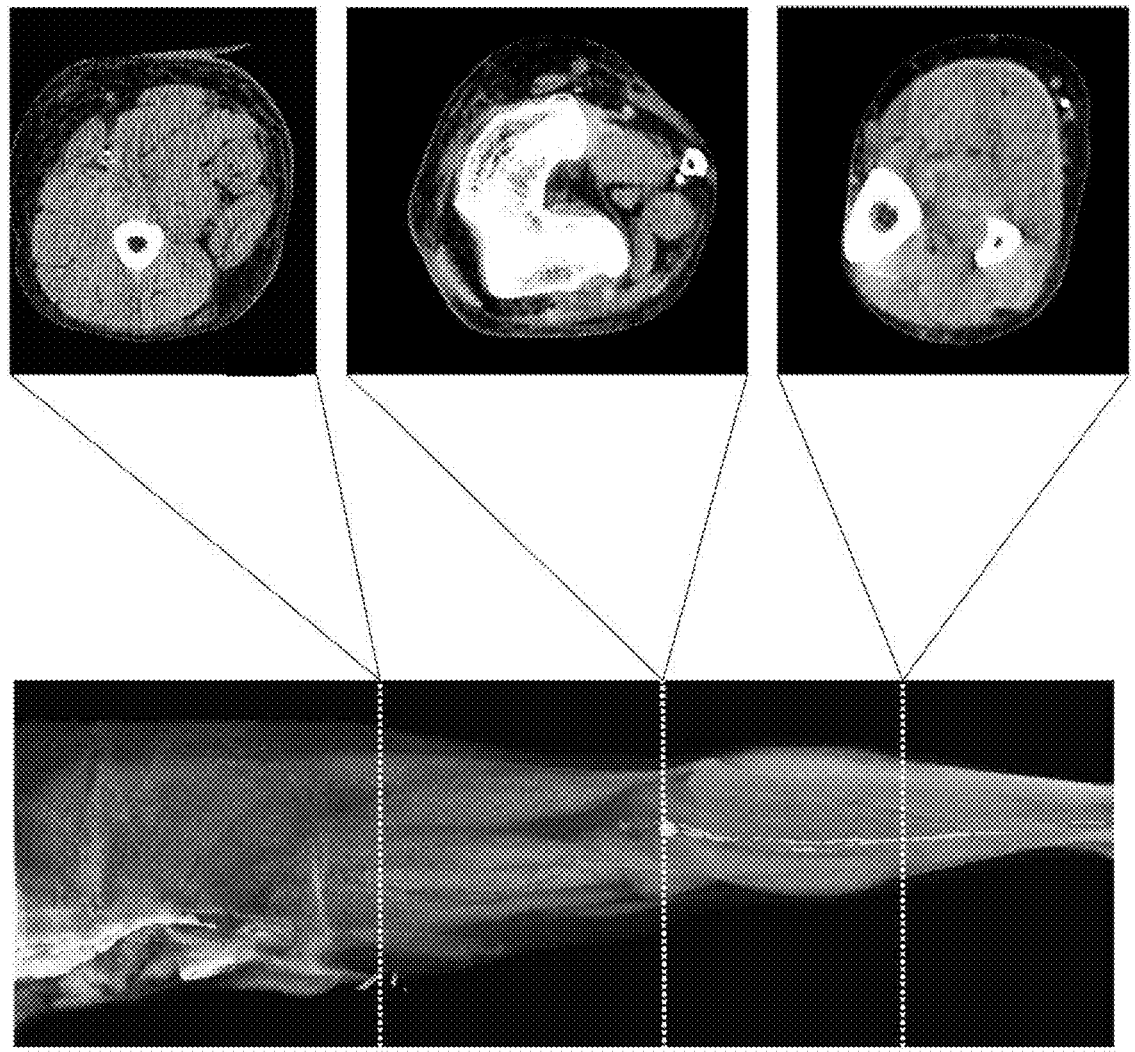

FIG. 26 is an image obtained by three-dimensionally constructing the CT lymphangiography image showing the traveling of the lymphatic route upon imaging the posterolateral route.

Figure 27:
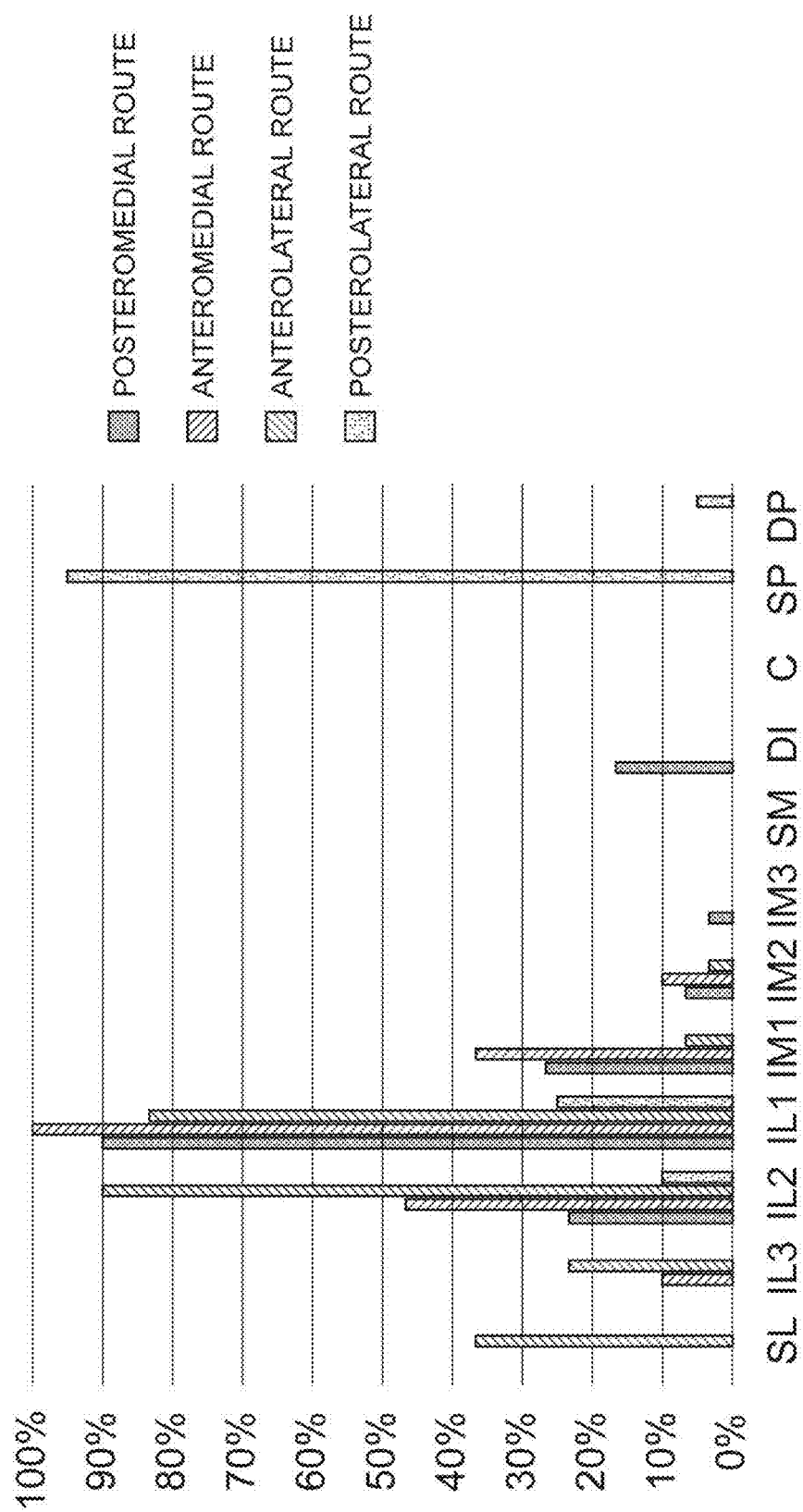

FIG. 27 is a graph plotting the frequency at which the posterolateral route reaches the first lymph nodes.

Figure 28:
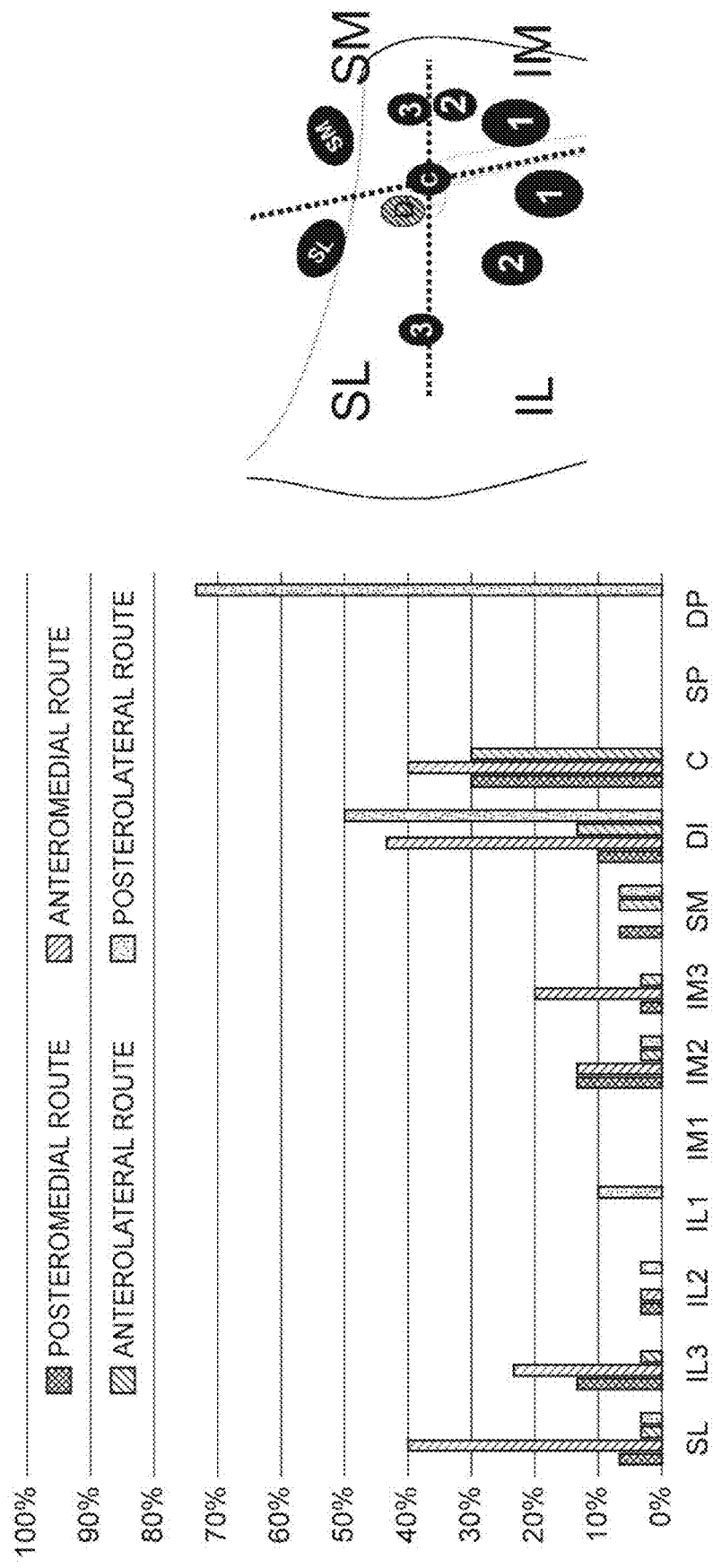

FIG. 28 is a graph plotting the frequency at which each lymphatic route of the lower limb reaches the second and following lymph nodes (lymph nodes that each lymphatic route reaches, other than the first lymph nodes that the lymphatic route reaches).

Figure 29A:
Figure 29B:

FIG. 29A is a photograph showing an example of a lymphangiography examination result of an upper limb. FIG. 29B is a trace diagram of FIG. 29A.

Figure 30:
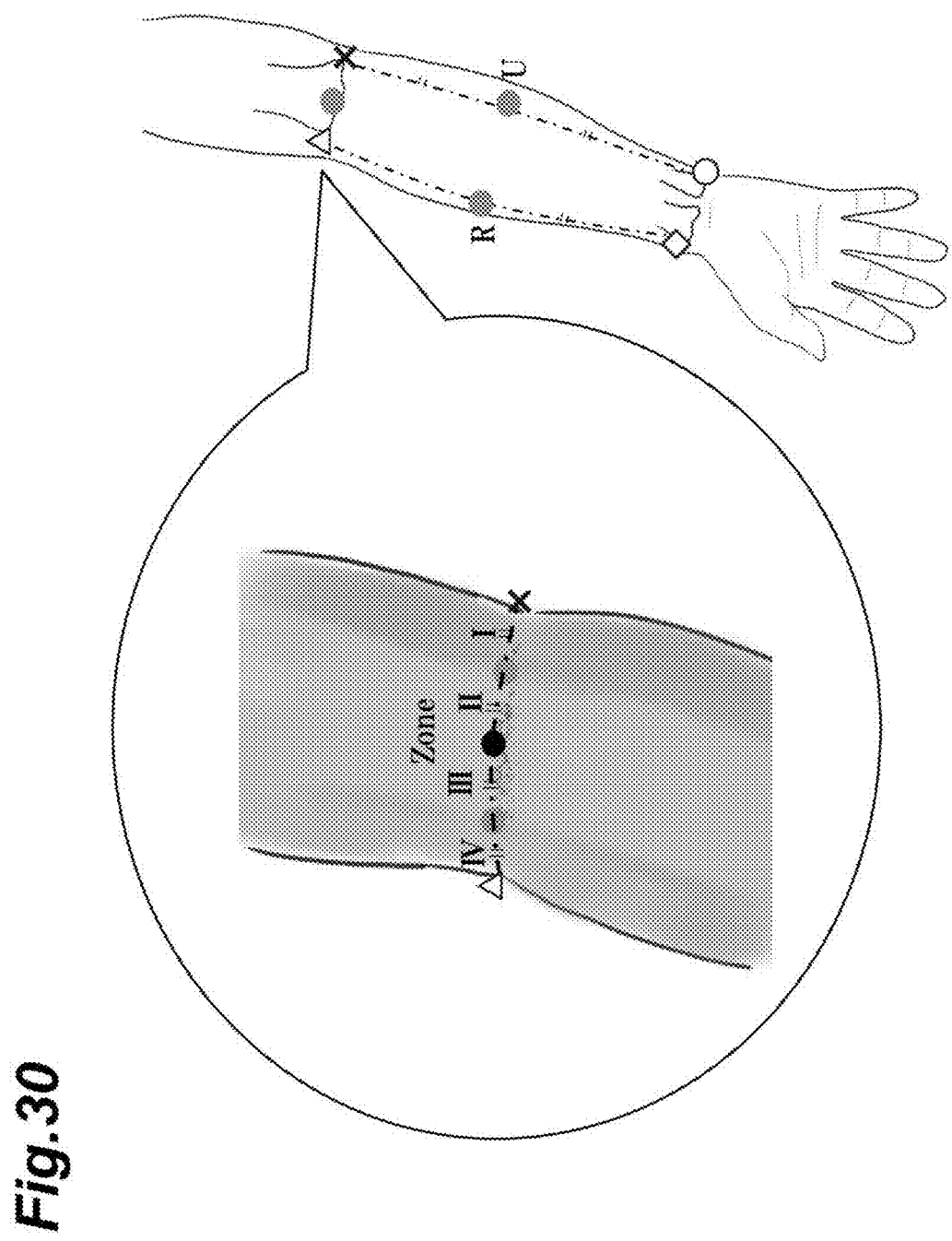

FIG. 30 is a diagram showing a definition of an upper limb region for describing the traveling of the lymphatic route.

Figure 31:
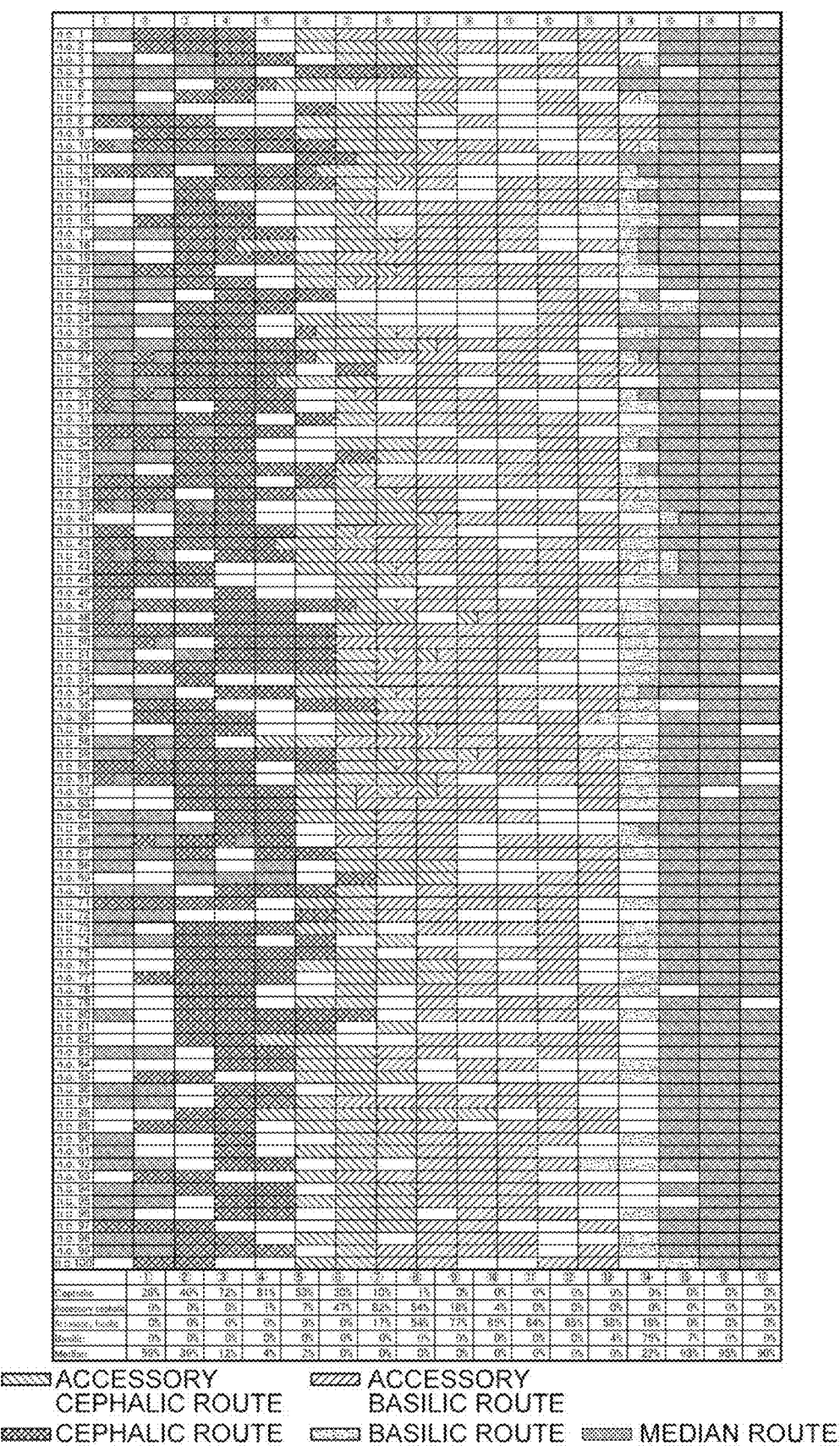

FIG. 31 shows a mapping of the relationship between the upper limb injection sites 1 to 17 in each body donation and the upper limb lymphatic routes (accessory cephalic route, accessory basilic route, cephalic route, basilic route, and median route) corresponding to each upper limb injection site.

Figure 32:
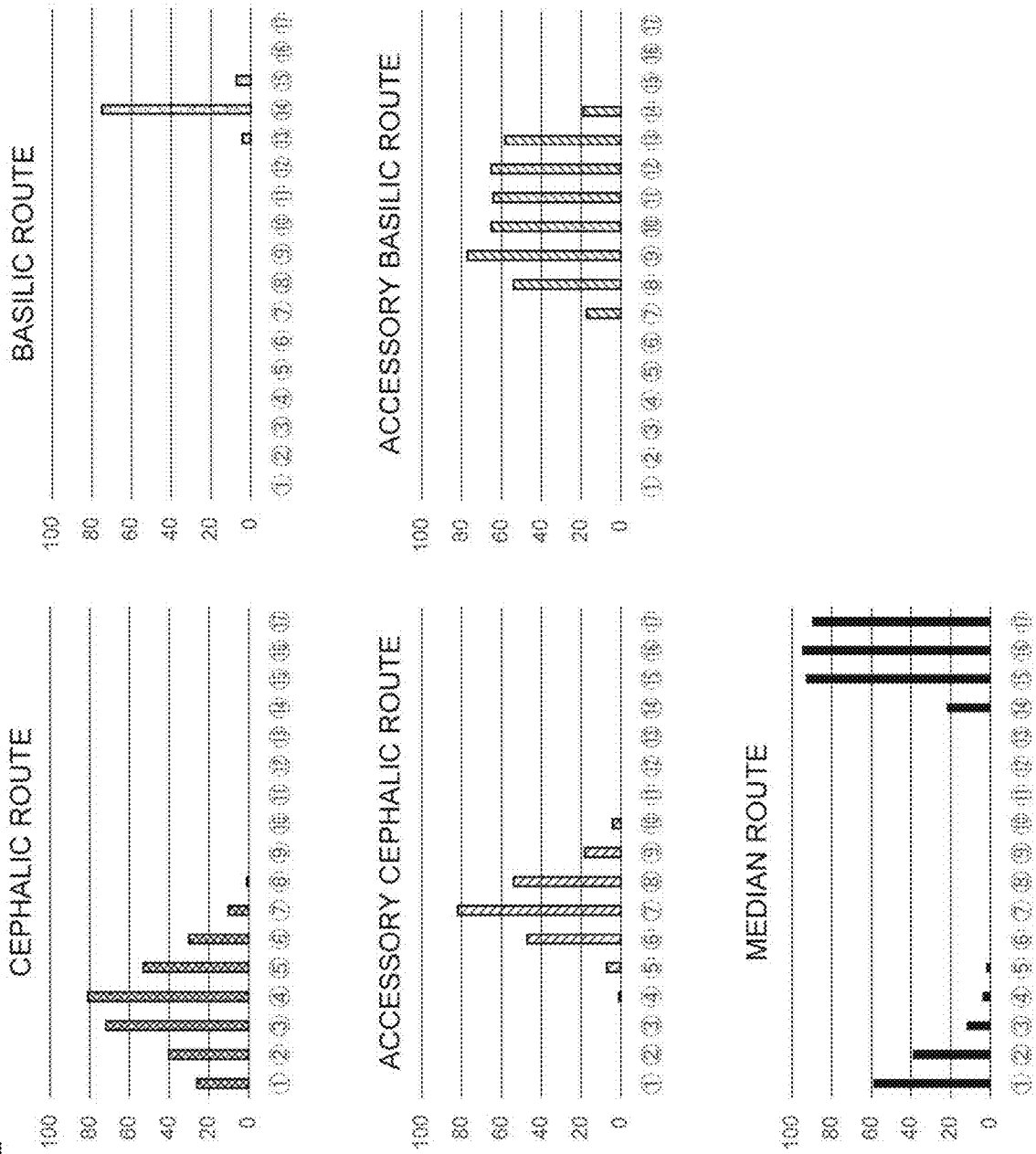

FIG. 32 shows the frequency (the number of body donations that could be imaged/the total number of body donations) at which the imaging can be made for each upper limb injection site, for each lymphatic route (accessory cephalic route, accessory basilic route, cephalic route, basilic route, and median route).

FIG. 33 is a schematic diagram showing a mapping of the regions occupied by each lymphatic route (accessory cephalic route, accessory basilic route, cephalic route, basilic route, and median route) in the upper limb.

DETAILED DESCRIPTION

Hereinafter, embodiments will be described in detail. However, the embodiments are not limited thereto, and can be variously modified in accordance with the gist thereof.

[Method of Evaluating Lymphatic System Function]

A method of evaluating a lymphatic system function includes the steps of: selecting one or a plurality of lymphatic routes to be evaluated from a plurality of lymphatic routes existing in four limbs; determining an injection site of a visualization agent based on information on the selected lymphatic route and injection sites of peripheries of four limbs corresponding to the selected lymphatic route; injecting the visualization agent from the selected injection site; and visualizing the injected visualization agent and evaluating functions of the one or plurality of lymphatic routes to be evaluated.

The "lymphatic system" in this specification includes lymph nodes, lymphatic vessels and other lymphatic tissues (for example, thoracic duct, thymus, spleen and the like).

The selecting step is a step of selecting one or a plurality of lymphatic routes to be evaluated from a plurality of lymphatic routes existing in the four limbs.

The lymphatic vessels constituting the lymphatic system often form independent lymphatic routes (lymphatic pathways) that do not communicate with each other in four limbs (in particular, below four limbs). In the selecting step, one or a plurality of lymphatic routes to be evaluated are selected. In the selecting step, a plurality of lymphatic routes may be selected so as to cover all independent lymphatic routes which do not communicate with each other as the evaluation target.

In the selecting step, one or a plurality of lymphatic routes to be evaluated may be selected from an anteromedial route, an anterolateral route, a posteromedial route, and a posterolateral route of the lower limb.

The anteromedial route, the anterolateral route, the posteromedial route, and the posterolateral route of the lower limb are lymphatic routes of the lower limb which are named according to a region through which the lymphatic vessels pass at an ankle joint level of the lower limb when the lower limb is divided into four regions at an ankle joint level. Here, with anterior edge of lateral malleolus and posterior edge of medial malleolus as a boundary, a heel side is "posterior" and the opposite side thereto is "anterior". With calcaneal tuberosity and an anterior midpoint between the anterior edge of the medial malleolus and the posterior edge of the lateral malleolus as a boundary, the medial malleolus is "medial" and the lateral malleolus is "lateral". The anteromedial route means the lymphatic route of the lower limb along which the lymphatic vessel passes through the regions of "anterior" and "medial" at the ankle joint level of the lower limb. Similarly, the anterolateral route means the lymphatic route of the lower limb along which the lymphatic vessel passes through regions of "anterior" and "lateral" at the ankle joint level of the lower limb. The posteromedial route means the lymphatic route of the lower limb along which the lymphatic vessel passes through the regions of "posterior" and "medial" at the ankle joint level of the lower limb. The posterolateral route means the lymphatic route of the lower limb along which the lymphatic vessel passes through the regions of "posterior" and "lateral" at the ankle joint level of the lower limb.

The selecting step may also select one or a plurality of lymphatic routes to be evaluated from a median route, a cephalic route, an accessory cephalic route, a basilic route, or an accessory basilic route of the upper limb.

The median route, the cephalic route, the accessory cephalic route, the basilic route, or the accessory basilic route of the upper limb are the lymphatic route of the upper limb which is named based on classification of upper limb cutaneous veins traveling substantially corresponding to each lymphatic route.

In the selecting step, all of the anteromedial route, the anterolateral route, the posteromedial route, and the posterolateral route of the lower limb may be selected as evaluation targets. By doing so, it is possible to comprehensively evaluate the function of the lymphatic vessels and the lymph nodes of the lower limbs. Similarly, in the selecting step, all of the median route, the cephalic route, the accessory cephalic route, the basilic route, and the accessory basilic route of the upper limb may be selected as the evaluation targets. By doing so, it is possible to comprehensively evaluate the functions of the lymphatic vessels and the lymph nodes of the upper limbs.

The determining step is a step of determining the injection site of the visualization agent based on information on the selected lymphatic route and injection sites of peripheries of four limbs corresponding to the selected lymphatic route.

Conventionally, there was no information that can understand the relationship between the injection site of the visualization agent and the lymphatic route to be imaged by taking in the visualization agent correspondingly. In the embodiment, as specifically shown in the Examples to be described later, a mapping of the corresponding relationship between the injection site of the visualization agent set based on the anatomical information and the lymphatic route to be imaged by taking in the visualization agent correspondingly succeeded (for example, FIGS. 1, 15 and 16, and FIGS. 2, 31 and 32). Based on the information (for example, the correspondence relationships shown in FIGS. 15 and 16 and FIGS. 31 and 32) or information conforming thereto (for example, information acquired for further specimen), it is possible to determine the injection site obtained by visualizing the selected lymphatic route.

In the determining step, only one injection site may be selected for one selected lymphatic route and determined as the injection site of the visualization agent, or two or more injection sites are selected and determined as the injection site of the visualization agent. As shown in the embodiment to be described later, for example, in the anteromedial route and the anterolateral route of the lower limb, there are two lower limb injection sites where the probability that the visualization agent (contrast medium) is taken in exhibits a peak (maximum value). For example, one of these lower limb injection sites may be selected as the injection site of the visualization agent, and both of these lower limb injection sites may be selected as the injection site of the visualization agent (it is to be noted that the lower limb injection site other than these lower limb injection sites may be selected as the injection site of the visualization agent).

For example, in the selecting step, when the lymphatic route of the lower limb is selected, the injection site of the visualization agent may be one or a plurality of injection sites selected from the lower limb injection sites 1 to 19 shown in FIG. 1 and may be one or a plurality of injection sites selected from the lower limb injection sites 1, 7, 14 and 16 shown in FIG. 1.

In addition, for example, in the selecting step, when all of the anteromedial route, the anterolateral route, the posteromedial route, and the posterolateral route of the lower limb are selected as the evaluation targets, the injection site of the visualization agent may be the lower limb injection sites 1, 7, 14, and 16 shown in FIG. 1. All of the lower limb injection sites 1, 7, 14, and 16 are set to be the injection sites of the visualization agent, so that it is possible to comprehensively evaluate all the four lymphatic routes of the lower limb.

In addition, for example, in the selecting step, when the lymphatic route of the upper limb is selected, the injection site of the visualization agent may be one or a plurality of injection sites selected from the upper limb injection sites 1 to 17 shown in FIG. 2 or may be one or a plurality of injection sites selected from the upper limb injection sites 4, 7, 9, 14 and 16 shown in FIG. 2.

In addition, for example, in the selecting step, when all of the median route, the cephalic route, the accessory cephalic route, the basilic route, or the accessory basilic route of the upper limb are selected as the evaluation target, the injection site of the visualization agent may be the upper limb injection sites 4, 7, 9, 14, and 16 shown in FIG. 2. All of the upper limb injection sites 4, 7, 9, 14, and 16 are set to be the injection sites of the visualization agent, so that it is possible to comprehensively evaluate all the five lymphatic routes of the upper limb.

The visualization agent is not particularly limited as long as administration to a human body is permitted. In addition, an appropriate visualization agent may be selected depending on the visualization method (detection method). As the visualization agent, for example, the contrast medium (for example, lipiodol, indocyanine green, $^{99m}$Tc-labeled tin colloid or the like) used in the conventional lymphography examination method can be used. As the visualization agent, in addition to the conventional contrast medium, for example, other dyes (for example, patent blue), fluorescent dye (for example, indigo carmine), and radioisotope labeled compounds (for example, $^{99m}$Tc-labeled technetium human serum albumin) can also be used.

The injecting step is a step of injecting the visualization agent from the selected injection site.

The method of injecting a visualization agent is not particularly limited, and a method similar to the conventional method of injecting a contrast medium can be adopted. For example, a method of injecting a visualization agent dissolved or suspended in an appropriate solvent such as physiological saline and buffer solution into an injection site using a syringe, or the like can be adopted.

The evaluating step is a step of visualizing the injected visualization agent and evaluating the functions of one or a plurality of lymphatic routes to be evaluated.

The method of visualizing a visualization agent may be selected according to a type of visualization agents to be used. For example, when the fluorescent dyes (for example, indocyanine green, lipiodol, patent blue, indigo carmine) are adopted as the visualization agent, it is possible to perform visualization and data collection by an infrared observation camera system including a light source (or filter) capable of exciting and fluorescently detecting the fluorescent dye. Examples of the infrared observation camera system can include PDE (manufactured by Hamamatsu Photonics K. K.), Hyper Eye Medical System (manufactured by Mizuho Co., Ltd.), LIGHTVISION (manufactured by Shimadzu Corporation), and SPY system (manufactured by Novadaq Technologies Inc.) and the like. In addition, for example, when the radioisotope labeled compound (for example, $^{99m}$Tc-labeled tin colloid, $^{99m}$Tc-labeled phytate, $^{99m}$Tc-labeled technetium human serum albumin) is used as the visualization agent, the visualization and the data collection can be performed by a radiation detector. Examples of the radiation detector can include a gamma camera, a single-photon emission computed tomography (SPECT) apparatus, a positron emission tomography (PET) apparatus, a SPECT-CT apparatus and the like.

As a result of visualizing the injected visualization agent, if the lymphatic route is not visualized, the reason that the lymphatic vessel disappears, lymph cannot move inside the lymphatic vessel, and the like can be considered, so that it can be determined that the function of the lymphatic system (lymphatic vessel) is damaged. In addition, as a result of visualizing the injected visualization agent, when the lymphatic route different from the assumed lymphatic route is visualized from the injection site, the reason that the assumed lymphatic route is somewhat damaged, the visualized lymphatic route becomes an alternative route, and the like can be considered, so that it can be determined that the function of the lymphatic system (lymphatic vessel) is damaged similar to the above. In addition, for example, as a result of visualizing the injected visualization agent, when a reflow of the lymph from the assumed lymphatic route is observed, it can be determined that the lymphatic route is damaged.

In addition, since the lymphatic vessels are connected to other lymphatic tissues such as lymph nodes, according to the method according to the embodiment, it is possible to selectively visualize not only the lymphatic vessels but also the lymph nodes, and even other lymphatic tissues. Therefore, for example, when the lymph node is not visualized, the reason that the lymph node disappears, the lymphatic vessel and the lymph node are disconnected, and the like can be considered, so that it can be determined that the functions of the lymphatic system (lymph node and lymphatic vessel) are damaged.

The method according to the embodiment can be applied to diagnosis of diseases such as primary lymphedema, secondary lymphedema, venous edema, and disuse edema, confirmation of therapeutic effect, diagnosis of prognosis and the like. The method according the embodiment can also be applied to reverse mapping for prevention of lymphedema after lymphadenectomy, for example.

[Apparatus of Evaluating Lymphatic System Function]

According to an embodiment, an apparatus of evaluating a lymphatic system function is used as a system of evaluating a lymphatic system function by combining with an imaging device. Examples of the imaging device may include a fluorescence detector and a radiation detector.

FIG. 3 is a block diagram showing a schematic configuration of a system 1 of evaluating a lymphatic system function according to an embodiment. The system 1 of evaluating a lymphatic system function shown in FIG. 3 includes a camera unit 7 (fluorescence detector) having an imaging device 3 and a light irradiation device 5 built therein, and an apparatus D of evaluating a lymphatic system function.

(Camera Unit)

The light irradiation device 5 includes a light source 5a that outputs excitation light $L_1$ for exciting a fluorescent dye for fluorescence observation of an observation object P (for example, a subject), and a light source control unit 5b that controls an output of the excitation light $L_1$ of the light source 5a. The light source 5a is a light emitting element such as a light emitting diode (LED), a laser diode (LD), and a super luminescent diode (SLD) and a lamp light source such as a halogen lamp and a xenon lamp, and outputs light of a wavelength at which the fluorescent dye is excited. For example, when the fluorescent dye is ICG, since a peak of an absorption wavelength of the fluorescent dye is around 800 nm in a body, as the light source 5a, a light source whose output light has a wavelength of, for example, 700 nm to 810 nm is used. A light source control unit 5b includes a light irradiation control circuit (for example, a processor) that controls the output and the output intensity (irradiation intensity) of the excitation light $L_1$ of the light source 5a under the control of the light irradiation control unit (not shown) which is electrically connected. It is preferable that the wavelength of the light output from the light source 5a does not include a wavelength of fluorescence, but when the wavelength of the light output from the light source 5a includes the wavelength of fluorescence, the light irradiation device 5 may include an optical filter (not shown) that shields light having the same wavelength as the wavelength of the fluorescence among the light output from the light source 5a.

The light irradiation control unit sets light irradiation conditions related to excitation light irradiation by the light irradiation device 5. The light irradiation control unit controls the light source control unit 5b so as to irradiate the excitation light under the set light irradiation conditions. The light irradiation control unit is a light irradiation control circuit (for example, a processor) for setting light irradiation conditions and controlling the light source control unit 5b. The light irradiation control unit may be built in the apparatus D for evaluating a lymphatic system function.

The imaging device 3 is a device that captures an image of the observation light $L_2$ including fluorescence from the observation object P under the control of an imaging control unit (not shown). The imaging device 3 includes an optical filter 3a that transmits light including the wavelength of fluorescence emitted from the fluorescent dye and shields light having the wavelength of the excitation light $L_1$, an image sensor 3b that receives the observation light $L_2$ transmitting the optical filter 3a and outputs image data by performing photoelectric conversion on the received observation light $L_2$, and an image sensor control unit 3c that controls exposure timing, exposure time, and signal readout of the image sensor 3b under the control of the imaging control unit. The image sensor control unit 3c is an imaging control circuit (for example, a processor) that controls a frame rate, exposure timing, exposure time, signal readout, and the like of the image sensor 3b under the control of the imaging control unit. The image sensor 3b is an area image sensor such as a CCD image sensor or a CMOS image sensor, and has a light receiving surface constituted by a plurality of pixels (photoelectric conversion elements) two-dimensionally arranged. The image sensor 3b is capable of variably adjusting the exposure time under the control of the image sensor control unit 3c.

The imaging control unit is the imaging control circuit (for example, a processor) that controls the operation of the imaging device 3. Specifically, for example, the imaging control unit sets the imaging conditions such as the exposure time, the exposure timing, and the frame rate of the image sensor 3b, and controls the image sensor control unit 3c so as to perform imaging based on the set imaging conditions. Examples of the image sensor 3b may include a CCD image sensor, a global shutter type CMOS image sensor, a rolling shutter type CMOS image sensor, and the like. The exposure time may be adjusted by an electronic shutter of the CCD image sensor or the CMOS image sensor and by controlling opening and closing of a physical aperture, a shutter or the like provided between the observation object P and the image sensor 3b or by adjusting an opening and closing amount of the physical aperture, the shutter or the like. The imaging control unit may also be built in the apparatus D for evaluating a lymphatic system function.

By the camera unit 7 configured as described above, the image sensor 3b receives (captures) the observation light $L_2$ including the fluorescence from the observation object P, and outputs the image data correspondingly. The apparatus D of evaluating a lymphatic system function acquires the image data (visualization agent image of a subject into which the visualization agent is injected) by a second acquisition means.

(Apparatus of Evaluating Lymphatic System Function)

The configuration of the apparatus D of evaluating a lymphatic system function will be described. FIG. 4 is a schematic diagram showing a hardware configuration of the apparatus D of evaluating a lymphatic system function according to an embodiment, and FIG. 5 is a schematic diagram showing a functional configuration of the apparatus D of evaluating a lymphatic system function according to an embodiment.

As shown in FIG. 4, the apparatus D of evaluating a lymphatic system function physically includes a main storage device such as CPU D11, ROM D12 and RAM D13, an input device D14 such as a keyboard, a mouse, and a touch screen, an output device D15 such as a display (including a touch screen), a communication module D16 such as a network card for transmitting and receiving data to and from other devices such as the camera unit 7 (fluorescence detector), and an auxiliary storage device D17 such as a hard disk, and is configured as an ordinary computer. The respective functions of the apparatus D of evaluating a lymphatic system function, which will be described later, are realized by reading predetermined computer software on the hardware such as the CPU D11, the ROM D12, and the RAM D13 to operate the input device D14, the output device D15, the communication module D16 and read and write data in the main storage devices D12 and D13 and the auxiliary storage device D17 under the control of the CPU D11.

As shown in FIG. 5, the apparatus D of evaluating a lymphatic system function includes a first acquisition means D1, a second acquisition means D2, a color setting means D3, and an output means D4 as functional structural elements. In addition, the apparatus D of evaluating a lymphatic system function may further include, as functional structural elements, an imaging control unit that controls the imaging device and/or a light irradiation control unit that controls the light irradiation device.

The first acquisition means D1 is for acquiring the information on the injection site of the visualization agent in the peripheries of the four limbs of the subject. For example, by displaying the figures as shown in FIG. 1 on the output device and inputting numbers corresponding to the injection sites into which the visualization agent is injected based on numbers in FIG. 1 from the input device, the first acquisition means acquires the information on the injection sites of the visualization agent the peripheries of the four limbs of the subject. In addition, for example, in the case where the output device is constituted by a touch screen, by displaying the figures as shown in FIG. 1 on the touch screen and touching the injection site into which the visualization agent is injected, the first acquisition means may acquire the information on the injection site of the visualization agent in the peripheries of the four limbs of the subject.

The second acquisition means D2 is for acquiring the visualization agent image (for example, a fluorescence image) of the subject into which the visualization agent is injected. For example, the second acquisition means acquires the visualization agent image (for example, a fluorescence image and a radiation image) output from the imaging device.

Based on the information acquired by the first acquisition means and the information on the plurality of lymphatic routes existing in the four limbs and the injection sites of the peripheries of the four limbs corresponding to the lymphatic routes, the color setting means D3 sets different colors on the visualization agent image acquired by the second acquisition means for each of the plurality of lymphatic routes existing in four limbs. For example, the lymphatic route in the lower limb can be classified into at least four lymphatic routes (anteromedial route, anterolateral route, posteromedial route, and posterolateral route), and the lymphatic route through which the visualization agent flows differs depending on the injection sites of the visualization agent. Therefore, based on the information on the injection site of the visualization agent and the information (for example, the information on the correspondence relationships shown in FIGS. 1, 15 and 16 and the equivalent information (for example, the information acquired for the further specimen)) of the lymphatic route of the lower limb and the injection site of the peripheries of the lower limb corresponding thereto, the color setting means sets the visualization agent image (for example, the anteromedial route is blue, the anterolateral route is green, the posteromedial route is purple, the posterolateral route is red, and the like) to be colors corresponding to each lymphatic route. By doing so, it is easy to visually grasp each lymphatic route and the lymphatic system can be easily evaluated. In addition, for example, the lymphatic route in the upper limb can be classified into at least five lymphatic routes (median route, cephalic route, accessory cephalic route, basilic route, and accessory basilic route), and the lymphatic route through which the visualization agent flows differs depending on the injection sites of the visualization agent. Therefore, based on the information on the injection site of the visualization agent and the information (for example, the information on the correspondence relationships shown in FIGS. 2, 31 and 32 or the equivalent information (for example, the information acquired for the further specimen)) of the lymphatic route of the upper limb and the injection site of the upper limb corresponding thereto, the color setting means sets the visualization agent image to be colors (for example, the median route is pink, the cephalic route is purple, the accessory cephalic route is blue, the basilic route is red, the accessory basilic route is green, and the like) corresponding to each lymphatic route. By doing so, it is easy to visually grasp each lymphatic route and the lymphatic system can be easily evaluated.

The output means D4 is for outputting the visualization agent image with a color by the color setting means. The visualization agent image with a color may be output to the output device or may be output from the communication module to other devices or may be output to the auxiliary storage device for recording.

[Program for Evaluating Lymphatic System Function]

The program for evaluating a lymphatic system function allows a computer to function as the first acquisition means D1, the second acquisition means D2, the color setting means D3, and the output means D4 which will be described above. By loading the program for evaluating a lymphatic system function on the computer, the computer can function as the apparatus D of evaluating a lymphatic system function. The program of evaluating a lymphatic system function is provided by being stored in a computer-readable storage medium, for example. The storage medium may be a non-transitory storage medium. Examples of the storage medium may include a storage medium such as a flexible disk, a CD, and a DVD, a storage medium such as an ROM, a semiconductor memory, and the like.

(Method of Evaluating Lymphatic System Function)

A method of evaluating a lymphatic system function performed by the apparatus D of evaluating a lymphatic system function will be described. First, the first acquisition means D1 is for acquiring the information on the injection site of the visualization agent in the peripheries of the four limbs of the subject. Next, the second acquisition means D2 is for acquiring the visualization agent image of the subject into which the visualization agent is injected. The acquisition of the information by the first acquisition means D1 and the second acquisition means D2 may be in reverse order.

Next, based on the information acquired by the first acquisition means and the information (for example, the information on the correspondence relationships shown in FIGS. 1, 15 and 16, and FIGS. 2, 31, and 32, or the equivalent information (for example, information acquired for further specimen and the like)) on the plurality of lymphatic routes existing in the four limbs and the injection sites of the peripheries of the four limbs corresponding thereto, the color setting means D3 sets different colors on the visualization agent image acquired by the second acquisition means for each of the plurality of lymphatic routes existing in four limbs. Next, the output means D4 is for outputting the visualization agent image with a color by the color setting means. For example, the visualization agent image (for example, a fluorescence image) of the lymphatic system of the subject of which the respective lymphatic routes are colored differently is displayed or the like by the output means D4.

EXAMPLE

Hereinafter, embodiments will be described more specifically based on test examples. All of the following tests were carried out under the approval of the ethics committee of Okayama University Hospital (K1605-020).

Test Example 1: Mapping of Lymphatic Route of Lower Limb

<Material and Method>

Indocyanine green (ICG) lymphangiography examination was performed on 100 (55 are male and 45 are female) lower limbs of 53 fresh human corpses. We obtained written informed consent in advance from all donors.

(ICG Lymphangiography Examination)

25 mg of indocyanine green (Diagnogreen (registered trademark), manufactured by Daiichi Sankyo Co., Ltd.) was dissolved in 10 mL of pure water. By using an injection needle (30 G), 0.05 mL of ICG solution was injected into the subcutaneous layer of each of the lower limb injection sites 1 to 19 shown in FIG. 1 (19 injection sites/1 lower limb).

The lower limb injection sites 1 to 19 shown in FIG. 1 were set on the boundary line of the dorsum pedis-planta pedis according to the anatomical landmark. Details of each lower limb injection site are shown as follows.

Lower limb injection site 1: Below medial malleolus
Lower limb injection site 5: Head of first metatarsal bone
Lower limb injection site 6: Base of first proximal phalanx)
Lower limb injection site 7: First interdigital part
Lower limb injection site 8: Second interdigital part
Lower limb injection site 9: Third interdigital part
Lower limb injection site 10: Fourth interdigital part
Lower limb injection site 11: Base of fifth proximal phalanx)
Lower limb injection site 12: Head of fifth metatarsal bone
Lower limb injection site 16: Below lateral malleolus
Lower limb injection site 18: Calcaneal tuberosity
Lower limb injection site 3: Midpoint between lower limb injection site 1 and lower limb injection site 5
Lower limb injection site 2: Midpoint between lower limb injection site 1 and lower limb injection site 3
Lower limb injection site 4: Midpoint between lower limb injection site 3 and lower limb injection site 5
Lower limb injection site 14: Midpoint between lower limb injection site 12 and lower limb injection site 16
Lower limb injection site 13: Midpoint between lower limb injection site 12 and lower limb injection site 14
Lower limb injection site 15: Midpoint between lower limb injection site 14 and lower limb injection site 16
Lower limb injection site 17: Midpoint between lower limb injection site 16 and lower limb injection site 18
Lower limb injection site 19: Midpoint between lower limb injection site 18 and lower limb injection site 1

Immediately after the injection of the ICG solution, the injection site was gently massaged by hand. The fluorescence image of the ICG was photographed by the infrared observation camera system (excitation wavelength of 760 nm, fluorescence wavelength of 830 nm). An image photographed by a slider of the infrared observation camera system was synthesized with an image composite editor (manufactured by Microsoft Corporation) to obtain a panoramic picture set with different colors for each lymphatic route.

<Results>

(Classification of Lymphatic Route of Lower Limb)

FIG. 6A is a photograph (panoramic picture) showing an example of the lymphangiography examination result of the lower limb. FIG. 6B is a trace diagram of FIG. 6A. The lower limb was divided into four regions (anterior medial side, anterior lateral side, posterior medial side, and posterior lateral side) at the ankle joint level. "Anterior" and "posterior" were defined based on the posterior edge of the lateral malleolus (indicated by "x") and the anterior edge of the medial malleolus (indicated by "Δ"). The heel side using "x" and "Δ" as the boundary is "posterior", and an opposite side thereto is "anterior". The "medial" and the "lateral" were defined based on the calcaneal tuberosity (indicated by "○") and the anterior midpoint (indicated by "□") between the anterior edge of the medial malleolus and the posterior edge of the lateral malleolus. The medial malleolus side using "○" and "□" as the boundary is "medial", and the lateral malleolus side is "lateral".

The lymphatic vessels of the lower limb were found to be roughly divided into four lymphatic routes of the anteromedial route, the posterolateral route, the anterolateral route, and the posteromedial route, depending on the position where the lymphatic vessel passes at the ankle joint level. In FIG. 6B, each lymphatic route (anteromedial route, posterolateral route, anterolateral route, or posteromedial route) is distinguished by different types of hatching.

(Detailed Analysis of Each Lymphatic Route)

1. Anteromedial Route

FIG. 7A is a photograph showing an example of results obtained by imaging the anteromedial route. FIG. 7B is a trace diagram of FIG. 7A. "□" indicates the anterior midpoint between the anterior edge of the medial malleolus and the posterior edge of the lateral malleolus, and "◇" indicates the midpoint between "□" and the tibial tuberosity. The anteromedial route coincides with the anteromedial bundle which can be recognized conventionally, and the appearance rate was 100% (100/100).

The anteromedial route originates from most of the dorsum pedis part, and many branches and fusions are repeated at the dorsum pedis part, but after the ankle joint (centrum side from the ankle joint), the branch fusion is reduced. At the ankle joint level, the anteromedial route becomes a clear bundle and passes through the anterior medial side (100%: 100/100). There were only a few examples where the anteromedial route spreads to the anterior lateral side or the posterior medial side at the ankle joint level (4%: 4/100).

The anteromedial route draws an arc outward below a lower leg, and draws an arc upward above the lower leg, so that the anteromedial route is directed upward while drawing sigmoid. The anteromedial route spreads to the anterior lateral side at the midpoint of the lower leg and passes therethrough is rare (15%: 15/100). The anteromedial route moves to the posterior medial side in the middle of the lower leg and passes from the inside to the posterior face at a knee joint, so that the anteromedial route is directed upward in the middle of the lower leg in a form of climbing over the great saphenous vein.

2. Posterolateral Route

The posterolateral route coincides with the posterolateral bundle which can be recognized conventionally, and the appearance rate was 92% (92/100).

The posterolateral route started from the outside of the heel part and passed through the posterior lateral sides as one or two straight lines at the ankle joint level (98.91%: 91/92). There were only a few examples where the posterolateral route spreads to a region other than the posterior lateral side at the ankle joint level (4.4%: 4/92).

The posterolateral route is directed upward to the vicinity of the popliteal fossa, and then moves to a deep part of a femoral region. Examples in which the posterolateral route is directed upward along a surface layer inside the femoral region from the popliteal fossa to the inguinal region were also observed at times. Examples in which the posterolateral route connects with the posteromedial route, or anterolateral route was rarely observed (7.6%: 4/92).

3. Anterolateral Route

FIG. 8A is a photograph showing an example of results obtained by imaging the anterolateral route. FIG. 8B is a trace diagram of FIG. 8A. "x" indicates the posterior edge of the lateral malleolus, "□" indicates the anterior midpoint between the anterior edge of the medial malleolus and the posterior edge of the lateral malleolus, and "◊" indicates the midpoint between "□" and the tibial tuberosity. The anterolateral route was located outside the anteromedial route (anteromedial bundle), and the appearance rate was 87% (87/100).

The anterolateral route originates from the outside of the dorsum pedis part and has a clearly independent beginning part (blind end) from the anteromedial route. At the ankle joint level, the anterolateral route is directed upward along the anterior lateral side as one or two straight lines and passes through a region distant from the bundle of the anteromedial route.

Most of the anterolateral route is directed upward along the anterior lateral side in the lower leg, but may be spread to the posterior lateral side at times. The anterolateral route finally moves to the anterior medial side, but moves to the anterior medial side under the midpoint of the lower leg (11.5%: 10/87), moves to the anterior medial side between the midpoint of the lower leg and the tibial tuberosity (49.4%: 43/87), and moves to the anterior medial side above the tibial tuberosity (39.1%: 34/87).

The anterolateral route is close to the anteromedial route at the femoral region but does not intersect with the anteromedial route and the relative positional relationship between the anterolateral route and the anteromedial route does not change. A few examples in which the anterolateral route is connected to the anteromedial route were observed (17.2%: 17/87).

4. Posteromedial Route

FIG. 9A is a photograph showing an example of results obtained by imaging the posteromedial route. FIG. 9B is a trace diagram of FIG. 9A. "Δ" indicates the anterior edge of the medial malleolus. The posterolateral route was located inside the anteromedial route (anteromedial bundle), and the appearance rate was 95% (95/100).

The posteromedial route originates from the center of the foot side portion and has a beginning part (blind end) independent of the anteromedial route. The posteromedial route is directed linearly on the lower leg or is directed upward in an arc toward the anterior side. The posteromedial route mostly falls in a lower side (deep direction of a foot) of the anteromedial route in the lower leg (69.47%: 66/95). The posteromedial route was a route along the great saphenous vein.

The details of the connection between the posteromedial route and the anteromedial route could not be observed because both routes are intersect with each other. However, it was confirmed that both routes were connected to each other at least several points in the lower leg.

FIGS. 10 to 13 are photographs obtained by photographing the lymphatic vessel of the lower leg by injecting the dye into the lymphatic vessel and dissecting the lymphatic vessel. It can be understood from FIG. 10 that the posteromedial route (indicated by the solid arrow) is along the great saphenous vein trunk (indicated by the dashed arrow) and that the anteromedial route (indicated by the arrow head) does not accompany the great saphenous vein trunk (indicated by the dashed arrow). It can be understood from FIG. 11 that the anteromedial route (indicated by the arrow head) accompanies the great saphenous vein branch (indicated by the dashed arrow). It can be better understood from FIG. 12 that when the anteromedial route (indicated by the arrow head) is turned over, the posteromedial route (indicated by the solid arrow) is accompanied along the great saphenous vein trunk (indicated by the dashed arrow). It can be better understood from FIG. 13 that the posteromedial route (indicated by the solid arrow) exists immediately above the fascia. FIG. 14A and FIG. 14B are schematic summaries of what is understood from FIGS. 10 to 13 (FIG. 14B is a cross-sectional view of the lower limb). It can be understood from FIG. 14A and FIG. 14B that the posteromedial route is a main route along the great saphenous vein trunk, the anteromedial route, which was conventionally considered to be the main route, is a subroute along the great saphenous vein branch.

(Mapping of Beginning Part (Blind End) of Each Lymphatic Route below Lower Leg)

FIG. 15 is a table showing a mapping of the relationships between the lower limb injection sites 1 to 19 in each body donation and the lymphatic route (anteromedial route, posterolateral route, anterolateral route, or posteromedial route) of the lower limb corresponding to each lower limb injection site. FIG. 16 is a graph showing a frequency (the number of body donations that could be imaged/the total number of body donations) at which imaging can be made for each lower limb injection site, for each lymphatic route (anteromedial route, posterolateral route, anterolateral route, or posteromedial route).

As shown in FIGS. 15 and 16, the majority was the case in which the contrast medium was taken in only one lymphatic route for one lower limb injection site, but the case in which the contrast medium was taken in from one lower limb injection site to the two lymphatic routes rarely happened. On the other hand, the contrast medium was not taken into three or more lymphatic routes from one lower limb injection site.

As shown in FIGS. 15 and 16, the anteromedial route had a peak (maximum value) of the frequency at which the imaging was be made for the lower limb injection sites 7 and 10. The posterolateral route had a peak (maximum value) of the frequency at which the imaging could be made for the lower limb injection site 16. The anterolateral route had a peak (maximum value) of the frequency at which the imaging could be made for the lower limb injection sites 10 and 14. The posteromedial route had a peak (maximum value) of the frequency at which the imaging could be made onto the lower limb injection site 1.

<Discussion>

According to this test, it was found that the lymphatic route of the lower limb can be roughly divided into four lymphatic routes of the anteromedial route, the posterolateral route, the anterolateral route, and the posteromedial route. With regard to these four lymphatic routes, in particular, in the lower leg, joining between the respective lymphatic routes rarely occurs and the respective lymphatic routes existed independently.

In addition, the injection site of the contrast medium that can be obtained by imaging these four lymphatic routes is distributed for each lymphatic route on the boundary line of dorsum pedis-planta pedis, and the probability (frequency at which the imaging could be made) that the contrast medium is injected into each lymphatic route for each lower limb injection site became clear. FIG. 17 is a schematic diagram showing a mapping of regions occupied by each lymphatic route (anteromedial route, posterolateral route, anterolateral route, or posteromedial route) below the lower limb, based on the results of Test Example 1.

Since the joining between the respective lymphatic route in the lower leg rarely occurs, even if only one lymphatic route is imaged from the periphery of the lower limb as conventionally done, there is a high possibility that evaluation on other lymphatic routes is not sufficient. In particular, in the lymphedema in which the lymphatic vessel/lymph node degenerate and lymphatic route damage occurs, since there are many occurrences of significant medial edema, it is expected that there will be bias in the damaged lymphatic route. Therefore, it is thought that it is necessary to evaluate all possible lymphatic routes. Such evaluation is indispensable for lymphatico-venous anastomosis and lymph node transplantation where it is important to search for the remaining lymphatic vessels, lymph nodes and lymphatic routes. In addition, even with all lymphography methods, it is necessary to prepare examination protocols taking into consideration of the four independent lymphatic routes in the future.

Test Example 2: Imaging of Lymphatic Vessel of Lower Limb in Patient

<Method>

A patient was a 72-year-old female with secondary lymphedema (international society of lymphology (ISL) classification stage 2) in the right lower limb due to a lymphadenectomy in a pelvis and radiotherapy of a pelvis. There was no edema in the left lower limb (ISL classification stage 0).

The lymphangiography of the lower limb was performed on this patient in the same procedure as in the ICG lymphangiography examination of Test Example 1. The injection site of the contrast medium was determined with reference to the results (in particular, the results shown in FIGS. 1, 15 and 16) obtained in Test Example 1.

<Results and Discussion>

The imaged results are shown in FIG. 18A. FIG. 18B is a trace diagram of FIG. 18A. In FIG. 18B, each lymphatic route (anteromedial route, posterolateral route, anterolateral route, or posteromedial route) of the lower limb is distinguished by different line types. Anteromedial route: dashed line, posterolateral route: two dot line, anterolateral route: solid line, posteromedial route: broken line.

By injecting the contrast medium from the lower limb injection site 16 (see FIG. 1), the posterolateral route of the right lower limb can be imaged to the middle of the lower leg, but is changed to lymph fluid pool (dermal back flow) halfway. The posteromedial route of the right lower limb cannot be imaged from any of the lower limb injection sites, and when the contrast medium is injected into the lower limb injection site 1 (see FIG. 1), the lymph fluid pool was imaged from the injection site. After the contrast medium is injected into lower limb injection sites 1 and 16, the anteromedial and anterolateral routes were not imaged.

By injecting the contrast medium into the lower limb injection site 7, 10 and 16 (see FIG. 1) of the right lower limb, only the anterolateral route was imaged. The anteromedial route was missing. The anterolateral route was changed to the lymph fluid pool in the middle of the lower leg.

In Test Example 1, the appearance rate of the anteromedial route was 100%, and the anterolateral route was only imaged from the lower limb injection site 7 with the probability of 5%. It can be said from the above description that the fact that the anterolateral route was imaged from the lower limb injection site 7 and the anteromedial route was not imaged indicates an abnormal condition in this patient.

By injecting the contrast medium from the lower limb injection sites 1, 7, 10, 14 and 16, all the lymphatic routes of the patient's left lower limb was imaged without any trouble. As can be seen from the results shown in FIGS. 15 and 16, by injecting the contrast medium from the lower limb injection sites 1, 7, 14, and 16, all the lymphatic routes can be imaged.

Test Example 3: Imaging of Lymphatic Vessel and Lymph Node of Lower Limb

For the respective lymphatic routes (anteromedial route, posterolateral route, anterolateral route, and posteromedial route) of the lower limb defined in Test Example 1, (i) a lymph node that the lymphatic route reaches first, (ii) a second and following lymph nodes that the lymphatic route reaches, and (iii) traveling of each lymphatic route were analyzed.

<Method>

Computed tomography (hereinafter, CT) lymphography examination was performed on 120 lower limbs of fresh human corpses. We obtained written informed consent in advance from all donors.

(CT Lymphography Test)

For each lymphatic route, 30 lower limbs (a total of 120 at 4 lymphatic routes) were subjected to the CT lymphography examination. First, the ICG lymphangiography was performed and the CT contrast medium was directly injected into the identified lymphatic vessel to obtain an image of the CT lymphography. For the lymphography examination on all the lymphatic routes, an ICG solution was injected into the lower limb injection sites 1 to 19 shown in FIG. 1, and the lymphatic vessels were identified based on the anatomical features.

Immediately after the injection of the ICG solution, the injection site was gently massaged by hand. The fluorescence image of the ICG was photographed by the infrared observation camera system (excitation wavelength of 760 nm, fluorescence wavelength of 830 nm). The identified lymphatic vessels were dissected near the ankle joint. The CT contrast medium was a solution in which 5 ml of ethyl ester of iodinated poppy-seed oil fatty acid injection solution (Lipiodol (registered trademark), Guerbet Japan) is dissolved in 20 mL of diethyl ether. Using an injection needle (32 G), 2 mL of lipiodol solution was directly injected into the identified and dissected lymphatic vessels.

<Results>

FIG. 19 is a diagram showing a definition of a superficial lymph node group at an inguinal region in this specification (Reference: Földi's Textbook of Lymphology 3rd Edition for Physicians and Lymphedema Therapists, Editors: Michael Foldi, Ethel Foldi, Published Date: 30 Apr. 2012, Imprint: Urban & Fischer). As shown in FIG. 19, the superficial lymph node groups in the inguinal region are divided into (1) a inferior lateral group (IL1 to 3), (2) a inferior medial group (IM1 to 3), (3) an superior medial group (SM), (4) an superior lateral group (SL), and (5) a center group (C), with the great saphenous vein as a vertical axis, a horizon from the saphenous opening (joining of the femoral vein) as a horizontal axis. For IL and IM lymph node groups, those along the saphenous vein are defined as number 1 (IL1), those near the horizontal axis are defined as number 3 (IL3), and those therebetween are defined as number 2 (IL2).

(Posteromedial Route)

FIG. 20 is an image obtained by three-dimensionally constructing a CT lymphography image showing traveling of the lymphatic route upon imaging the posteromedial route. The lymphatic route is imaged in white color in three cross-sectional views of the lower limb. The posteromedial route ascends along a hem of tibial bone similar to the actual anatomical finding, and traveled on a layer just above the deep fascia. The posteromedial route ascended along sartorius muscle posterior edge in the femoral region. The posteromedial route traveled on a layer equal to or deeper than the great saphenous vein. The posteromedial route partially fell below the deep fascia at a distal femur part and traveled near a femoral artery. Traveling along the posteromedial route to join a deep system before reaching the lymph node is not found in other lymphatic routes. The posteromedial route generally corresponds to the traveling of the great saphenous vein trunk.

FIG. 21 is a graph plotting the frequency at which the posteromedial route reaches the first lymph nodes. As shown in FIG. 21, a lot of posteromedial routes reached IL1 lymph nodes. In addition, a portion of the posteromedial routes reached the IL2 lymph node and the IM1 to IM3 lymph nodes. In addition, although not happened often, some of the posteromedial routes directly joined with a deep inguinal lymph node (DI). Joining the DI is a feature not found in other lymphatic routes.

(Anteromedial Route)

FIG. 22 is an image obtained by three-dimensionally constructing a CT lymphography image showing traveling of the lymphatic route upon imaging the anteromedial route. The lymphatic route is imaged in white color in three cross-sectional views of the lower limb. The anteromedial route traveled to cross the hem of tibial bone at the lower leg. The anteromedial route traveled inside the sartorius muscle in the femoral region. The anteromedial route traveled on a layer equal to or shallower than the great saphenous vein trunk.

FIG. 23 is a graph plotting the frequency at which the anteromedial route reaches the first lymph nodes. As shown in FIG. 23, the distribution of the first lymph nodes that the anteromedial route reaches was similar to that of the posteromedial route, but the anteromedial route did not reach the deep inguinal lymph node (DI). In addition, the frequency at which the anteromedial route reaches the IL3 lymph node, the IL2 lymph node, the IM1 lymph node, and the IM2 lymph node was higher than that of the posteromedial route.

(Anterolateral Route)

FIG. 24 is an image obtained by three-dimensionally constructing a CT lymphography image showing traveling of the lymphatic route upon imaging the anterolateral route. The lymphatic route is imaged in white color in three cross-sectional views of the lower limb. The anterolateral route passed a front surface of the lower leg from the outside, and moved to the inside of the lower limb near the lower leg. The anterolateral route passed a front surface of the sartorius muscle in the femoral region.

FIG. 25 is a graph plotting the frequency at which the anterolateral route reaches the first lymph nodes. As shown in FIG. 25, the anterolateral route reached the IL2 lymph node most frequently and reached the IL1 lymph node second most frequently. In addition, a part of the anterolateral route reached an SL lymph node group. Reaching the SL lymph node group has a feature not found in other lymphatic routes.

(Posterolateral Route)

FIG. 26 is an image obtained by three-dimensionally constructing a CT lymphography image showing traveling on the lymphatic route upon imaging the posterolateral route. The lymphatic route is imaged in white color in three cross-sectional views of the lower limb. One or two posterolateral routes existed and ascended along a back surface of the lower leg. The posterolateral route entered below the fascia after joining a superficial popliteal lymph node below a knee and mostly ascended along the femoral artery. A portion of the posterolateral route released a branch to the anterior medial side or anterior lateral side group from the lower leg or below the knee, or occasionally in the middle of the femoral region.

FIG. 27 is a graph plotting the frequency at which the posterolateral route reaches the first lymph nodes. FIG. 27 plots the frequency at which other lymphatic routes reaches the first lymph nodes (that is, the plots of FIGS. 21, 23, and 25 are also merged). As shown in FIG. 27, the posterolateral route mostly reached the superficial popliteal lymph node (SP). A portion of the posterolateral route reached the IL2 lymph node or the IL1 lymph node by releasing the branch at the lower leg, below the knee, or in the femoral region.

The following Table 1 shows the frequency at which each lymphatic route of the lower limb reaches the first lymph nodes.

TABLE 1

|  | SP | DP | SL | IL3 | IL2 | IL1 | IM1 | IM2 | IM3 | SM | DI | C |
|---|---|---|---|---|---|---|---|---|---|---|---|---|
| Posteromedial route | 0% | 0% | 0% | 7% | 27% | 90% | 30% | 7% | 3% | 0% | 13% | 0% |
| Anteromedial route, | 0% | 0% | 0% | 13% | 40% | 100% | 37% | 10% | 0% | 0% | 0% | 0% |
| Anterolateral route | 0% | 0% | 40% | 23% | 93% | 83% | 7% | 3% | 0% | 0% | 0% | 0% |
| Posterolateral route | 87% | 13% | 0% | 0% | 10% | 20% | 0% | 0% | 0% | 0% | 0% | 0% |

FIG. 28 is a graph plotting the frequency at which each lymphatic route of the lower limb reaches the second and following lymph nodes (that is, lymph nodes that each lymphatic route reaches, other than the first lymph nodes that the lymphatic route reaches). As shown in FIG. 28, the posteromedial route reached the SL lymph node group, the IL3 lymph node, the IL2 lymph node, the IM2 lymph node, the IM3 lymph node, the SM lymph node group, the deep inguinal lymph node (DI), and a C lymph node group. As shown in FIG. 28, the anteromedial route reached the SL lymph node group, the IL3 lymph node, the IL2 lymph node, the IM2 lymph node, the IM3 lymph node, the deep inguinal lymph node (DI), and the C lymph node group. As shown in FIG. 28, the anterolateral route reached the SL lymph node group, the IL3 lymph node, the IM2 lymph node, the IM3 lymph node, the SM lymph node group, the deep inguinal lymph node (DI), and the C lymph node group. As shown in FIG. 28, the posterolateral route reached the SL lymph node, the IL2 lymph node, the IL1 lymph node, the IM2 lymph node, the SM lymph node group, the deep inguinal lymph node (DI), and a deep popliteal lymph node (DP).

As shown in FIG. 28, the anteromedial route reached the second and following lymph nodes most frequently. Among them, the frequency at which the anteromedial route reached the SL lymph node group is highest and there was the possibility that the anteromedial route reaches any of other lymph nodes. None of the lymphatic routes of the lower limb was almost likely to reach the second and following IL1 lymph node and IL2 lymph node.

<Discussion>

It was understood from the results of the comprehensive analysis on the lymphatic routes of the lower limb that the lymph from the peripheral side of the lower limb first reached any one of the IL1 lymph node, the IL2 lymph node, and the superficial popliteal lymph node at a high frequency. Since the frequency (possibility) at which the lymph from the peripheral side of the lower limb reached lymph nodes other than the IL1 lymph node, the IL2 lymph node, and the superficial popliteal lymph node among the superficial lymph node groups of the inguinal region rarely occurs, the lymph nodes other than the IL1 lymph node, the IL2 lymph node, and the superficial popliteal lymph node are estimated to play a supplementary role. In addition, the second and following lymph nodes that the lymph from the peripheral side of the lower limb reaches had a myriad of connections. From the results of Test Example 3, when evaluating the lymph nodes of the lower limb, by imaging the IL1 lymph node, the IL2 lymph node, and the superficial popliteal lymph node, it was understood that the overall function of the lymphatic system (lymph node and lymphatic vessel) from the periphery of the lower limb can be evaluated.

Conventionally, it was considered that all lymph nodes can be examined by injecting the contrast medium into one location at the time of the lymphography examination of the lower limb. However, it was understood from the result of Test Example 3 that each lymphatic route (the anteromedial route, posterolateral route, the anterolateral route, and the posteromedial route) of the lower limb does not necessarily coincide with main lymph nodes (first lymph nodes that the lymphatic route reaches) and there is a need to comprehensively analyze the lymphatic route of the lower limb in order to comprehensively evaluate the lymph nodes. In addition, among a myriad of inguinal lymph nodes, the main lymph nodes of the lower limb lymphatic system and other auxiliary lymph nodes can be divided for function evaluation.

Test Example 4: Mapping of Lymphatic Route of Upper Limb

<Material and Method>

The indocyanine green (ICG) lymphangiography examination was performed on 100 upper limbs of 53 fresh human corpses. We obtained written informed consent in advance from all donors.

(ICG lymphangiography Examination)

25 mg of indocyanine green (Diagnogreen (registered trademark), manufactured by Daiichi Sankyo Co., Ltd.) was dissolved in 10 mL of pure water. By using an injection needle (30 G), 0.05 mL of ICG solution was injected into the subcutaneous layer of each of the upper limb injection sites 1 to 17 shown in FIG. 2 (17 injection sites/1 upper limb).

The upper limb injection sites 1 to 17 shown in FIG. 2 were set on the boundary line of the dorsum manus-palmar according to the anatomical landmark. Details of each upper limb injection site are as follow.

Upper limb injection site 1: Distal of radial styloid process

Upper limb injection site 5: The first head of metacarpal bone

Upper limb injection site 3: Midpoint between upper limb injection site 1 and upper limb injection site 5

Upper limb injection site 2: Midpoint between upper limb injection site 1 and upper limb injection site 3

Upper limb injection site 4: Midpoint between upper limb injection site 3 and upper limb injection site 5

Upper limb injection site 6: The first interdigital space

Upper limb injection site 7: The second interdigital space

Upper limb injection site 8: The third interdigital space

Upper limb injection site 9: The fourth interdigital space

Upper limb injection site 10: The fifth head of metacarpal bone

Upper limb injection site 14: Distal of radial styloid process

Upper limb injection site 12: Midpoint between upper limb injection site 10 and upper limb injection site 14

Upper limb injection site 11: Midpoint between upper limb injection site 10 and upper limb injection site 12

Upper limb injection site 13: Midpoint between upper limb injection site 12 and upper limb injection site 14

Upper limb injection site 16: Midpoint between upper limb injection site 1 and upper limb injection site 14 (palmar side)

Upper limb injection site 15: Midpoint between upper limb injection site 14 and upper limb injection site 16

Upper limb injection site 17: Midpoint between upper limb injection site 16 and upper limb injection site 1

Immediately after the injection of the ICG solution, the injection site was gently massaged by hand. The fluorescence image of the ICG was photographed by the infrared observation camera system (excitation wavelength of 760 nm, fluorescence wavelength of 830 nm). An image photographed by the slider of the infrared observation camera system was synthesized with an image composite editor (manufactured by Microsoft Corporation) to obtain a panoramic picture set with different colors for each lymphatic route.

<Results>

(Classification of Lymphatic Route of Upper Limb)

FIG. 29A is a photograph (panoramic picture) showing an example of the lymphangiography examination result of the upper limb. FIG. 29B is a trace diagram of FIG. 29A. The lymphatic route of the upper limb is classified into a subgroup according to the anatomical traveling thereof. The lymphatic vessels of the upper limb travel towards the axillary lymph node, so that the lymphatic vessels are very dense on the upper arm. Therefore, the lymphatic vessels traveling from a wrist joint to an elbow was classified using the anatomical landmark. As a result, the lymphatic vessels could be divided into 5 subgroups: an accessory cephalic route, an accessory basilic route, a cephalic route, a basilic route, and a median route (see FIG. 29B). These lymphatic vessels were generally consistent with the traveling of the cutaneous vein, and therefore are named accordingly.

In addition, as the anatomical landmark, epicondylus medialis humeri (indicated by "x" in FIGS. 29 and 30), epicondylus lateralis humeri (indicated by "Δ" in FIGS. 29 and 30), radial styloid process (indicated by "□" in FIGS. 29 and 30), ulnar styloid process (indicated by "O" in FIGS. 29 and 30), and olecranon are used to classify the lymphatic routes. FIG. 30 is a diagram showing a definition of an upper limb region for describing the traveling of the lymphatic route. First, in a cubital fossa, a space between the epicondylus medialis humeri and the epicondylus lateralis humeri was divided into four equal parts, zones I, II, III and IV were divided in order from the inside, and a part of the olecranon other than the zones I to IV was set to be zone V, thereby classifying the traveling lymphatic routes. In addition, in the forearm, the midpoint between the epicondylus lateralis humeri and the radial styloid process (point R in FIG. 30) was set on the radial side, and the midpoint (point U in FIG. 30) between the epicondylus medialis humeri and the ulnar styloid process was set on the ulnar side, which was set as an indicator.

(Detailed Analysis of Each Lymphatic Route)

1. Accessory Cephalic Route

The accessory cephalic route primarily originates from the radial side of the dorsum manus and travels along the accessory cephalic vein. The appearance rate of the accessory cephalic route was 94% (94/100). In the accessory cephalic route, an average of 2.0 lymphatic vessels pass at the wrist joint level and ascends through a vicinity from the point R while generally drawing a loosely S-shaped curve on the radial side, and the lymphatic vessel passing through the zone IV in the cubital fossa was mainly used (96%: 86/90).

In addition, the case in which the lymphatic vessel passed through only the zone III (3%: 3/94) of the cubital fossa and the zone V (1%: 1/94) was recognized. In 11 limbs, there is a connection with the accessory basilic route on the forearm (11%: 11/100). In addition, 12 legs with routes connected to supraclavicular lymph nodes were recognized (12%: 12/100).

2. Cephalic Route

The cephalic route has a beginning part around a thumb metacarpals midpoint and travels along the cephalic vein. The appearance rate of the cephalic route was 99% (99/100). In the cephalic route, an average of 1.8 lymphatic vessels pass at the wrist joint level and turn around the dorsum manus side from the radial styloid process, and the lymphatic vessel that reaches the forearm flexion side at a distal part from the point R and reaches the upper arm through the cubital fossa zone III was mainly used (96%: 95/99). Those passing through the cubital fossa zone II were also recognized (4%: 4/99). A slightly bending side from the accessory cephalic route travels along the cephalic vein. Only three cases disappeared into the deep part through the lymph nodes between biceps brachii muscles after passing through the cubital fossa were recognized (3%: 3/95). In the upper arm, these cases overlap the lymphatic vessel of the median route, and therefore cannot be often distinguished by near infrared analysis (NIR).

3. Accessory Basilic Route

The accessory basilic route mainly originates from the ulnar side of the dorsum manus, turns around the ulnar styloid process and is curved in the direction of the forearm ulnar side to reach the bending side and ascends. The appearance rate of the accessory basilic route was 100% (100/100). In the accessory basilic route, an average of 2.8 lymphatic vessels passed through at the wrist joint level and the lymphatic vessel that passed through the cubital fossa zone I and reached the upper arm was mainly used (96%: 96/100). 40 limbs also coexisted with the lymphatic vessel ascending toward the upper arm through the zone V. Many lymphatic vessels of the accessory basilic route passed through both the proximal part and distal part of the forearm U and extensively traveled on the ulna side of the upper arm.

4. Basilic Route

The basilic route originates from a boundary part between the palmar side and the dorsum manus of the ulnar distal end and ascends the forearm along the basilic vein and passes through the cubital fossa zone I to reach the upper arm. The appearance rate of the basilic route was 81% (81/100). In the basilic route, one or two lymphatic vessels traveled and ascended while joining the lymphatic vessels of several accessory basilic routes on the forearm ulnar side.

5. Median Route

In the median route, the ventral side of the wrist joint serves as the beginning part, and an average of 4.8 lymphatic vessels passes at the wrist joint level, and ascends the median forearm. The appearance rate of the median route was 100% (100/100). The median route gradually converges to one or two lymphatic vessels and passes through the cubital fossa zone II to reach the upper arm. In the upper arm, the median route overlaps the cephalic route and ascends.

(Mapping of Beginning Part (Blind End) of Each Lymphatic Route in Upper Limb)

FIG. 31 is a table showing a mapping of the relationship between the upper limb injection sites 1 to 17 in each body donation and the lymphatic routes (accessory cephalic route, accessory basilic route, cephalic route, basilic route, and median route) of the upper limb corresponding to each upper limb injection sites. FIG. 32 shows the frequency (the number of body donations that could be imaged/the total number of body donations) at which the imaging can be made for each upper injection site, for each lymphatic route (accessory cephalic route, accessory basilic route, cephalic route, basilic route, and median route).

As shown in FIGS. 31 and 32, the lymphatic routes corresponding to each upper limb injection site was almost identical, and it was shown that each upper limb injection site was the origin of a specific lymphatic route. In addition, there was a case in which the contrast medium was taken into two lymphatic routes from one upper limb injection site, but no contrast medium was taken into three or more lymphatic routes. On the dorsal side of the upper limb, the accessory basilic route had the largest skin lymphatic territory, and on the ventral side of the upper limb, the median route had a large skin lymphatic territory. In the case in which the accessory cephalic route was developed, it was also recognized that the skin lymphatic territory of the accessory basilic route was small. Generally, the skin lymphatic territory of the cephalic route and the basilic route was small.

<Discussion>

As shown in FIGS. 31 and 32, the cephalic route had a peak (maximum value) of the frequency at which the imaging was be made for the upper limb injection site 4. The accessory cephalic route had a peak (maximum value) of the frequency at which the imaging could be made for the upper limb injection site 7. The accessory basilic route had a peak (maximum value) of the frequency at which the imaging could be made for the upper limb injection site 9. The basilic route had a peak (maximum value) of the frequency at which the imaging could be made for the upper limb injection site 14. The median route had a peak (maximum value) of the frequency at which the imaging could be made for the upper limb injection site 16. In addition, it is possible to detect all five lymphatic routes in the upper limb at these five upper limb injection sites. The anatomical specifications of these five upper limb injection sites are as follows: the midpoint (upper limb injection site 4) between the distal end of the radius and the head of the thumb metacarpal bone, the second interdigital (upper limb injection site 7), the fourth interdigital (upper limb injection site 9), and the boundary point (upper limb injection site 14) between the ventral side and the dorsum side of the distal end of the ulna, and the median of the ventral side of the wrist joint (upper limb injection site 16).

FIG. 33 is a schematic diagram showing a mapping of regions occupied by each lymphatic route (accessory cephalic route, accessory basilic route, cephalic route, basilic route, and median route) in the upper limb based on the results of Test Example 4.

In one embodiment, the lymphatic system may be pressurized by lymphatic massage or suppression stocking based on the results of the lymphatic system function evaluation by the system 1 of evaluating a lymphatic system function.

REFERENCE SIGNS LIST

1 . . . System of evaluating lymphatic system function, 3 . . . Imaging device, 3$a$ . . . Optical filter, 3$b$ . . . Image sensor, 3$c$ . . . Image sensor control unit, 5 . . . Light irradiation device, 5$a$ . . . Light source, 5$b$ . . . Light source control unit, 7 . . . Camera unit, D . . . Apparatus of evaluating lymphatic system function, P . . . Observation object, $L_1$ . . . Excitation light, $L_2$ . . . Observation light, D1 . . . First acquisition means, D2 . . . Second acquisition means, D3 . . . Color setting means, D4 . . . Output Means, D12, D13 . . . Main storage device, D14 . . . Input device, D15 . . . Output device, D16 . . . Communication module, D17 . . . Auxiliary storage device.

What is claimed is:

1. A method of evaluating a lymphatic system function, comprising:
   selecting one or a plurality of lymphatic routes to be evaluated from an anteromedial route, an anterolateral route, a posteromedial route, and a posterolateral route of a human lower limb;
   determining an injection site of a visualization agent based on information on the selected lymphatic route and injection sites of peripheries of human lower limbs corresponding to the selected lymphatic route;
   injecting the visualization agent from the selected injection site; and
   visualizing the injected visualization agent and evaluating, based on whether the visualization agent has passed through the selected lymphatic route, functions of the one or plurality of lymphatic routes,
   wherein the injection site of the visualization agent is three or more of injection sites selected from human lower limb injection sites 1, 7, 14, and 16 shown in FIG. 1.

2. The method according to claim 1, wherein in the selecting, all of the anteromedial route, the anterolateral route, the posteromedial route, and the posterolateral route of the human lower limb are selected as the lymphatic routes to be evaluated.

3. The method according to claim 1, wherein in the evaluating, when a reflow of the lymph from one or a plurality of lymphatic routes to be evaluated is observed, it is determined that the lymphatic route where the reflow is observed is damaged.

4. The method according to claim 1, wherein in the evaluating, when one or a plurality of lymphatic routes to be evaluated is not visualized and/or when different lymphatic routes are visualized, it is determined that the lymphatic function is in an abnormal state.

5. The method according to claim 1, further comprising:
   diagnosing a lymphatic disease based on the visualization of the injected visualization agent and evaluation of functions of the one or plurality of lymphatic routes.

* * * * *